(12) United States Patent
Lee et al.

(10) Patent No.: US 10,851,390 B2
(45) Date of Patent: Dec. 1, 2020

(54) METHOD FOR PRODUCING METAL NANOPARTICLES AND METAL SULFIDE NANOPARTICLES USING A RECOMBINANT MICROORGANISM

(71) Applicant: KOREA ADVANCED INSTITUTE OF SCIENCE AND TECHNOLOGY, Daejeon (KR)

(72) Inventors: Sang Yup Lee, Daejeon (KR); Yoojin Choi, Jeollabuk-do (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/068,475

(22) PCT Filed: Dec. 29, 2016

(86) PCT No.: PCT/KR2016/015498
§ 371 (c)(1),
(2) Date: Jul. 6, 2018

(87) PCT Pub. No.: WO2017/119671
PCT Pub. Date: Jul. 13, 2017

(65) Prior Publication Data
US 2019/0024124 A1 Jan. 24, 2019

(30) Foreign Application Priority Data

Jan. 8, 2016 (KR) .................. 10-2016-0002710
Dec. 29, 2016 (KR) .................. 10-2016-0182245

(51) Int. Cl.
| | | |
|---|---|---|
| *C12P 3/00* | (2006.01) | |
| *C07K 14/825* | (2006.01) | |
| *C12N 1/20* | (2006.01) | |
| *C01G 19/00* | (2006.01) | |
| *C01G 5/00* | (2006.01) | |
| *C01G 15/00* | (2006.01) | |
| *C01G 51/00* | (2006.01) | |
| *C01B 19/00* | (2006.01) | |
| *C01G 45/00* | (2006.01) | |
| *C01G 1/12* | (2006.01) | |
| *C01G 53/00* | (2006.01) | |
| *C12N 9/02* | (2006.01) | |
| *C01G 45/12* | (2006.01) | |
| *C01G 49/00* | (2006.01) | |
| *C12N 9/10* | (2006.01) | |

(52) U.S. Cl.
CPC .............. *C12P 3/00* (2013.01); *C01B 19/002* (2013.01); *C01G 1/12* (2013.01); *C01G 5/00* (2013.01); *C01G 15/00* (2013.01); *C01G 19/00* (2013.01); *C01G 45/00* (2013.01); *C01G 45/1235* (2013.01); *C01G 49/0063* (2013.01); *C01G 51/40* (2013.01); *C01G 53/40* (2013.01); *C07K 14/825* (2013.01); *C12N 1/20* (2013.01); *C12N 9/0051* (2013.01); *C12N 9/104* (2013.01); *C12Y 203/02015* (2013.01); *C01P 2002/72* (2013.01); *C01P 2002/82* (2013.01); *C01P 2004/04* (2013.01); *C01P 2004/64* (2013.01); *C01P 2006/40* (2013.01); *C01P 2006/42* (2013.01)

(58) Field of Classification Search
None
See application file for complete search history.

(56) References Cited

U.S. PATENT DOCUMENTS

| | | | |
|---|---|---|---|
| 2011/0124131 A1 | 5/2011 | Lee et al. | |
| 2015/0090313 A1 | 4/2015 | Schulz et al. | |

FOREIGN PATENT DOCUMENTS

| | | |
|---|---|---|
| JP | 2009541593 A | 11/2009 |
| JP | 2013013403 A | 1/2013 |
| KR | 100621309 B1 | 9/2006 |
| KR | 100755746 B1 | 8/2007 |
| KR | 100755746 B1 | 9/2007 |
| KR | 100896656 B1 | 5/2009 |
| KR | 101305554 B1 | 9/2013 |
| KR | 20150035426 A | 4/2015 |

OTHER PUBLICATIONS

Park, T.J., et al., "Advances in microbial biosynthesis of metal nanoparticles", "Appl Microbiol Biotechnol", Mar. 25, 2015, Page(s) DOI 10.1007/s00253-015-6904-7, Publisher: Springer.

(Continued)

*Primary Examiner* — Kagnew H Gebreyesus
(74) *Attorney, Agent, or Firm* — Hultquist, PLLC; Steven J. Hultquist

(57) ABSTRACT

The present invention relates to a method of producing metal nanoparticles and metal sulfide nanoparticles using a recombinant microorganism co-expressing metallothionein and phytochelatin synthase, which are heavy metal-adsorbing proteins, and to the use of metal nanoparticles and metal sulfide nanoparticles synthesized by the method. The present invention provides a method for synthesizing metal nanoparticles which have been difficult to synthesize by conventional biological methods. The present invention makes it possible to synthesize metal nanoparticles in an environmentally friendly and cost-effective manner, and also makes it possible to synthesize metal sulfide nanoparticles. In addition, even metal nanoparticles which could have been produced by conventional chemical or biological methods are produced in a significantly increased yield by use of the method of the present invention.

15 Claims, 18 Drawing Sheets
(7 of 18 Drawing Sheet(s) Filed in Color)
Specification includes a Sequence Listing.

(56) References Cited

OTHER PUBLICATIONS

Seo, J. M., et al., "BioSynthesis of Diverse Metal Nanoparticles and its Applications (P1012)", "Korean Society for Biotechnology and Bioengineering Fall Meeting and International Symposium", 2013, p. 333.

Bharadwaj, S., et al., "Characterization of Silver Tellurite", "Journal of Solid State Chemistry", 1989, pp. 256-265, vol. 80.

Bharde, A., et al., "Bacterial Enzyme Mediated Biosynthesis of Gold Nanoparticles", "J. Nanosci. Nanotechnol.", 2007, pp. 4369-4377, vol. 7, No. 12.

Fan, W., et al., "Semiconductor-based Nanocomposites for Photocatalytic H2 Production and CO2 Conversion", "Phys. Chem. Chem. Phys.", 2013, pp. 2632-2649, vol. 15, No. 8.

Gurunathan, S., et al., "Biosynthesis, Purification and Characterization of Silver Nanoparticles Using *Escherichia coli*", "Colloids and Surfaces B: Biointerfaces", 2009, pp. 328-335, vol. 74.

Hulkoti, N., et al., "Biosynthesis of Nanoparticles Using Microbes—A Review", "Colloids and Surfaces B: Biointerfaces", 2014, pp. 474-483, vol. 121.

Joo, J., et al., "Generalized and Facile Synthesis of Semiconducting Metal Sulfide Nanocrystals", "J. Am. Chem. Soc.", 2003, pp. 11100-11105, vol. 125.

Kalishwaralal, K., et al., "Biosynthesis of Silver and Gold Nanoparticles Using Brevibacterium Casei", "Colloids and Surfaces B: Biointerfaces", 2010, pp. 257-262, vol. 77.

Kang, S., et al., "Microbial Synthesis of CdS Nanocrystals in Genetically Engineered *E. coli*", "Biosynthesis of Nanoparticles", 2008, pp. 5186-5189, vol. 47.

Korbekandi, H., et al., "Production of Nanoparticles Using Organisms", "Critical Reviews in Biotechnology", 2009, pp. 279-306, vol. 29, No. 4.

Lee, K., et al., "In Vitro Biosynthesis of Metal Nanoparticles in Microdroplets", "ACS Nano", 2012, pp. 6998-7008.

Moghaddam, A., et al., "Nanoparticles Biosynthesized by Fungi and Yeast: A Review of Their Preparation, Properties, and Medical Applications", "Molecules", 2015, pp. 16540-16565, vol. 20.

Nies, D., "Microbial Heavy-Metal Resistance", "Appl. Microbiol. Biotechnol.", 1999, pp. 730-750, vol. 51.

Park, T., et al., "Advances in Microbial Biosynthesis of Metal Nanoparticles", "Appl. Microbiol. Biotechnol.", 2015, pp. 1-14.

Park, T., et al., "In Vivo Synthesis of Diverse Metal Nanoparticles by Recombinant *Escherichia coli*", "Angew. Chem. Int. Ed.", 2010, pp. 7019-7024, vol. 49.

Plaza, G., et al., "Biosurfactant Mediated Biosynthesis of Selected Metallic Nanoparticles", "Int. J. Mol. Sci", 2014, pp. 13720-13737, vol. 15.

Quester, K., et al., "Biosynthesis and Microscopic Study of Metallic Nanoparticles", "Micron", 2013, pp. 1-27.

Rui, X., et al., "Nanostructured Metal Sulfides for Energy Storage", "Nanoscale", 2014, pp. 9889-9924, vol. 6.

Sardar, M., et al., "Biosynthesis of Metal Nanoparticles and Their Applications", "Biosensors Nanotechnology", 2014, pp. 239-266.

Seo, J., et al., "Self-Assembly of Biogenic Gold Nanoparticles and Their Use to Enhance Drug Delivery Into Cells", "Colloids and Surfaces B: Biointerfaces", 2015, pp. 27-34, vol. 135.

Shedbalkar, U., et al., "Microbial Synthesis of Gold Nanoparticles: Current Status and Future Prospects", "Advances in Colloid and Interface Science", 2014, pp. 40-48, vol. 209.

Sriram, M., et al., "Biosynthesis of Silver and Gold Nanoparticles Using Bacillus licheniformis", "Methods Mol. Biol.", 2012, pp. 33-43, vol. 906.

Xui, Z., et al., "Negligible Particle-Specific Antibacterial Activity of Silver Nanoparticles", "Nano Letters", 2012, pp. 4271-4275, vol. 12.

METHOD FOR PRODUCING METAL NANOPARTICLES AND METAL SULFIDE NANOPARTICLES USING A RECOMBINANT MICROORGANISM

CROSS-REFERENCE TO RELATED APPLICATIONS

This is a U.S. national phase under the provisions of 35 U.S.C. § 371 of International Patent Application No. PCT/KR16/15498 filed Dec. 29, 2016, which in turn claims priority of Korean Patent Application No. 10-2016-0002710 filed Jan. 8, 2016 and Korean Patent Application No. 10-2016-0182245 filed Dec. 29, 2016. The disclosures of International Patent Application No. PCT/KR16/15498 and Korean Patent Application Nos. 10-2016-0002710 and 10-2016-0182245 are hereby incorporated herein by reference, in their respective entireties, for all purposes.

TECHNICAL FIELD

The present invention relates to a method of producing metal nanoparticles and metal sulfide nanoparticles using a recombinant microorganism, and more particularly to a method of producing metal nanoparticles and metal sulfide nanoparticles using a recombinant microorganism co-expressing metallothionein and phytochelatin synthase, which are heavy metal-adsorbing proteins.

BACKGROUND ART

As interest in nanotechnology has increased, various studies have been actively conducted to develop nanometer-sized new materials in various fields, including as physics, chemistry, materials, electricity, and electronics. In particular, materials comprising metal nanostructures can be applied to the fabrication of high-efficiency electronic, optics, photoelectronics, electronic devices, bioactive molecule detection devices, and catalysts, which were difficult to realize by bulk materials made using existing technologies, and these materials can also be applied in medicines, cosmetics, energy conversion and storage, etc., indicating that these materials are used in various and broad applications (Shedbalkar U et al., *Adv Colloid Interface Sci*, 209: 40-48, 2014; Fan W et al., *Phys Chem Chem Phys*, 15(8): 2632-2649, 2013; Korbekandi H et al., *Crit Rev Biotechnol* 29(4):279-306, 2009). Thus, studies have been actively conducted to synthesize novel metal nanoparticles or to discover the novel properties of existing metal nanoparticles.

In the production of conventional metal nanoparticles, a chemical method of synthesizing the metal nanoparticles from a metal element using a chemical reducing agent has been mainly used. However, this method has disadvantages in that it requires a toxic organic solvent and a costly catalyst and requires high temperature and high pressure conditions, and thus it causes environmental pollution problems and has low energy efficiency and economic efficiency. For this reason, as an environmentally friendly and cost-effective alternative, biological methods using organisms having reductase have been proposed. In fact, cases have been reported in which metal nanoparticles are synthesized from metal elements using microorganisms, enzymes, plants, or the like (Paza G A et al., *Int J Mol Sci* 15(8):13720-13737, 2014; Hulkoti N I et al., *Colloids Surf B Biointerfaces*, 121:474-483, 2014; Moghaddam et al., *Molecules*, 20(9): 16540-16565, 2015; Park T J et al., *Appl Microbiol Biotechnol*, 1-14, 2015). However, such methods use the biological mechanisms of organisms themselves without changes, and have a limitation in that elements that are applied for the synthesis of nanoparticles are limited to gold, silver, copper, cadmium, iron, selenium and the like (Quester K et al., *Micron*, 54-55:1-27, 2013; Bharde A et al., *J Nanosci Nanotechnol*, 7(12):4369-4377. 2007; Shedbalkar U et al., *Adv Colloid Interface Sci*, 209:40-48, 2014; Sriram M I et al., *Methods Mol Biol*, 906:33-43, 2012; Gurunathan S et al., *Colloids Surf B Biointerfaces*, 74(1):328-335, 2009).

Previously, the present inventors produced metal nanoparticles from elements such as zinc (Zn), selenium (Se), tellurium (Te), cesium (Cs), copper (Cu), lead (Pb), nickel (Ni), manganese (Mn), mercury (Hg), cobalt (Co) and chromium (Cr) by use of recombinant microorganisms that express heavy metal-adsorbing protein (Lee et al., *ACS Nano* 6(8):6998-7008, 2012; Korean Patent No. 10-0755746). However, there were limitations in producing metal nanoparticles using various other metal elements, and there was a problem in that the yield is also low.

Meanwhile, metal sulfide nanoparticles are attracting attention as next-generation electrode materials and energy storage materials because of their unique and excellent characteristics (Rui X et al., *Nanoscale*, 6(17): 9889-9924, 2014). Accordingly, prior art technologies related to methods for producing metal sulfide nanoparticles have been reported, including a method of producing metal sulfide nanocrystals using a thiol compound as a sulfur precursor, which is related to a method of obtaining metal sulfide crystals by reacting a metal precursor with a thiol compound (Korean Patent No. 10-0621309); plate-like or linear indium composite nanomaterials for use as a buffer in a solar cell (Korean Patent No. 10-1305554); a method of producing tin sulfide nanoparticles by heating tin sulfide precursors and a method of fabricating a lithium ion battery using the same (Korean Patent No. 10-0896656), and the like. However, the above methods have disadvantages in that they require a high reaction temperature of 300° C. or higher, are not environmentally friendly due to the use of organic solvents such as toluene, and require a subsequent heat treatment process, which is disadvantageous in terms of production costs. In addition, CdS and PbS (Joo J et al., *J. Am. Chem. Soc*, 125(36):11100-11105, 2003), which are used as semiconductor materials, have negative environmental impacts, and thus it is required to synthesize metal sulfide nanoparticles using elements other than cadmium- or lead-based metal sulfides.

Accordingly, the present inventors have made extensive efforts to produce various metal nanoparticles and metal sulfide nanoparticles which have not been synthesized in conventional art. As a result, the present inventors have found that, when culture conditions are optimized using a recombinant microorganism co-expressing metallothionein and phytochelatin synthase, which are heavy metal-adsorbing proteins, metal nanoparticles and metal sulfide nanoparticles can be produced from elements which have not been reported as elements for synthesis of metal nanoparticles in conventional art, and the yield of metal nanoparticles which have been produced by conventional methods is also significantly increased, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide a method of producing single-element metal nanoparticles using a recombinant microorganism.

Another object of the present invention is to provide a method of producing metal alloy nanoparticles using a recombinant microorganism.

Still another object of the present invention is to provide a method of producing metal sulfide nanoparticles using a recombinant microorganism.

Yet another object of the present invention is to provide the use of the produced metal nanoparticles.

Technical Solution

To achieve the above object, the present invention provides a method for producing a single-element metal nanoparticle, comprising the steps of: (a) culturing a recombinant microorganism into which a metallothionein-encoding gene and a phytochelatin synthase-encoding gene are introduced; (b) adding to a medium of step (a) a metal ion selected from the group consisting of zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), yttrium (Y), aluminum (Al), and europium (Eu), followed by additional culturing, thereby producing a single-element metal nanoparticle; and (c) recovering the produced single-element metal nanoparticle.

The present invention also provides a method for producing a metal alloy nanoparticle, comprising the steps of: (a) culturing a recombinant microorganism into which a metallothionein-encoding gene and a phytochelatin synthase-encoding gene are introduced; (b) adding to a medium of step (a) two or more metal ions selected from the group consisting of zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), yttrium (Y), aluminum (Al), and europium (Eu), followed by additional culturing, thereby producing a metal alloy nanoparticle; and (c) recovering the produced metal alloy nanoparticle.

The present invention also provides a method for producing a metal sulfide nanoparticle, comprising the steps of: (a) culturing a recombinant microorganism into which a metallothionein-encoding gene and a phytochelatin synthase-encoding gene are introduced; (b) adding to a medium of step (a) a metal ion selected from the group consisting of i) zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), yttrium (Y), aluminum (Al), and europium (Eu); and ii) sulfur, followed by additional culturing, thereby producing a metal sulfide nanoparticle; and (c) recovering the produced metal sulfide nanoparticle.

The present invention also provides a contrast agent comprising a silver tellurite ($Ag_2TeO_3$) nanoparticle.

The present invention also provides an electrode comprising a silver tellurite ($Ag_2TeO_3$) nanoparticle.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
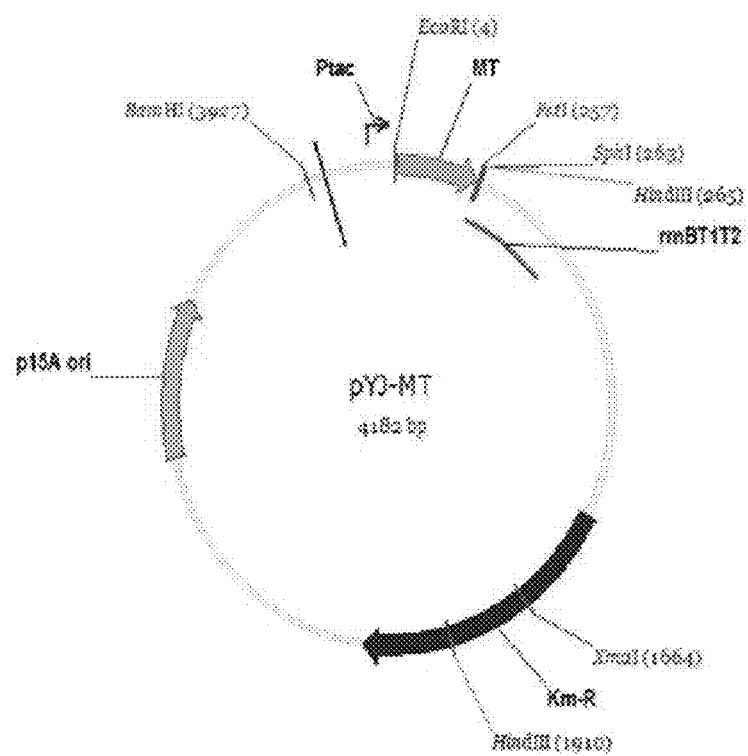
FIG. 1 is a genetic map of the expression vector pYJ-MT according to the present invention.

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In the present invention, in order to synthesize various metal nanoparticles using a biological method, a recombinant microorganism co-expressing two heavy metal-adsorbing proteins (metallothionein and phytochelatin synthase) was cultured in media containing various metal elements. As a result, it was found that single-element metal nanoparticles were synthesized.

In one example of the present invention, a recombinant microorganism was cultured, and then additionally cultured in medium containing a single-element metal ion such as barium (Ba), zirconium (Zr), molybdenum (Mo), indium (In), tin (Sn), lanthanum (La), cerium (Ce) or praseodymium (Pr), and as a result, it could be seen that amorphous single nanoparticles were synthesized. Meanwhile, when the recombinant microorganism was cultured in medium containing cobalt (Co), nickel (Ni), zinc (Zn) or cadmium (Cd) ions, it was observed that single-element metal nanoparticles were not synthesized. However, when the recombinant microorganism was cultured in media containing these metal ions after increasing the pH of the media, it could be seen that crystalline metal particles of cobalt oxide ($Co_3O_4$), nickel hydroxide ($Ni(OH)_2$), zinc oxide (ZnO) or cadmium hydroxide ($Cd(OH)_2$) were produced. In addition, when the recombinant microorganism was cultured in medium containing lanthanum (La), cerium (Ce), praseodymium (Pr), neodymium (Nd), samarium (Sm), europium (Eu) or gadolinium (Gd) ions, it was observed that amorphous single-element metal nanoparticles were synthesized. However, when the recombinant microorganism was cultured in media containing the above-described metal ions after increasing the pH of the media, it was observed that crystalline single-element metal nanoparticles of lanthanum hydroxide ($La(OH)_3$), cerium oxide ($CeO_2$), praseodymium hydroxide ($Pr(OH)_3$), neodymium hydroxide ($Nd(OH)_3$), samarium hydroxide ($Sm(OH)_3$), europium hydroxide ($Eu(OH)_3$) or gadolinium hydroxide ($Gd(OH)_3$) were produced.

Therefore, in a first aspect, the present invention is directed to a method for producing single-element metal nanoparticles, comprising the steps of: (a) culturing in a medium a recombinant microorganism having introduced therein a metallothionein-encoding gene and a phytochelatin synthase-encoding gene; (b) adding to the medium of step (a) a metal ion selected from the group consisting of zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), yttrium (Y), aluminum (Al), and europium (Eu), followed by additional culturing, thereby producing single-element metal nanoparticles; and (c) recovering the produced single-element metal nanoparticles.

In the present invention, the added metal ion may be selected from the group consisting of zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), yttrium (Y), aluminum (Al), and europium (Eu), but is not limited thereto.

In the present invention, the produced metal nanoparticles may be selected from the group consisting of cobalt oxide ($Co_3O_4$), nickel hydroxide ($Ni(OH)_2$), zinc oxide peroxide (ZnO), cadmium hydroxide ($Cd(OH)_2$), cobalt hydroxide ($Co(OH)_2$), barium carbonate ($BaCO_3$), lanthanum hydroxide ($La(OH)_3$), cerium oxide ($CeO_2$), praseodymium hydroxide ($Pr(OH)_3$), neodymium hydroxide ($Nd(OH)_3$), samarium hydroxide ($Sm(OH)_3$), europium hydroxide ($Eu(OH)_3$), cerium hydroxide ($Ce(OH)_3$), yttrium hydroxide ($Y(OH)_3$), aluminum hydroxide ($Al(OH)_3$), and gadolinium hydroxide ($Gd(OH)_3$), but are not limited thereto.

In the present invention, it could be found that the surface functional groups of the single-element metal nanoparticles comprise 3300-3000 $cm^{-1}$ (OH groups), 2960-2850 $cm^{-1}$ (C—H), 1650-1660 $cm^{-1}$ (amide I), 1540-1535 $cm^{-1}$ (amide II), 1240-1234 $cm^{-1}$ (amide III), and 1150-1030 $cm^{-1}$ (C=O) in an IR spectrum range of 400 to 4000 $cm^{-1}$.

In the present invention, when the culture in step (b) was performed after adjusting the initial pH to 7.3 to 7.7, it could be seen that the metal nanoparticles were produced with the highest efficiency while the pH increased to 8.0 to 9.0 with the passage of time. In addition, it could be seen that the potential (Eh) of the medium when the metal nanoparticles were produced with the highest efficiency was −0.5 V to +0.5 V.

Thus, in the present invention, the pH of the medium in step (b) may be adjusted so that it reaches an optimal pH of 8.0-9.0 at which the single-element metal nanoparticles are produced by additional culture of the recombinant microorganism.

To this end, the initial pH of the medium in step (b) before additional culture is preferably increased to 7.3 to 7.7, more preferably 7.4 to 7.6.

In the present invention, the initial pH of the medium in step (a) before culture may be 6 to 7, preferably 6.4 to 6.6.

When the pH in the microorganism culture step and the pH in the metal nanoparticle production step are adjusted as described above, it is possible to synthesize metal nanoparticles which have been difficult to synthesize in conventional art. Metal nanoparticles that can be synthesized by increasing the pH may be selected from the group consisting of cobalt oxide ($Co_3O_4$), nickel hydroxide ($Ni(OH)_2$), zinc oxide (ZnO) and cadmium hydroxide ($Cd(OH)_2$), but are not limited thereto.

In addition, the single-element metal nanoparticles including cobalt oxide($Co_3O_4$), nickel hydroxide ($Ni(OH)_2$), zinc oxide peroxide (ZnO), cadmium hydroxide ($Cd(OH)_2$), lanthanum hydroxide ($La(OH)_3$), cerium oxide ($CeO_2$), praseodymium hydroxide ($Pr(OH)_3$), neodymium hydroxide ($Nd(OH)_3$), samarium hydroxide ($Sm(OH)_3$), europium hydroxide ($Eu(OH)_3$), and gadolinium hydroxide ($Gd(OH)_3$) were amorphous when the pH was not adjusted, but crystalline nanoparticles were produced as the pH was increased.

In another example of the present invention, the recombinant microorganism was cultured, and then it was observed that i) metal alloy nanoparticles of cobalt iron oxide ($CoFe_2O_4$) were produced in a medium containing cobalt and iron (Co, $CoCl_2$, 0.5 mM, Fe, $Fe(NO_3)_3 \cdot 6H_2O$, 0.5 mM); ii) metal alloy nanoparticles of nickel iron oxide ($NiFe_2O_4$) were produced in a medium containing nickel and iron (Ni, $NiCl_2 \cdot 6H_2O$, 0.5 mM, Fe, $Fe(NO_3)_3 \cdot 6H_2O$, 0.5 mM); iii) metal alloy nanoparticles of zinc manganese oxide ($ZnMn_2O_4$) were produced in a medium containing zinc and manganese (Zn, $ZnSO_4 \cdot 7H_2O$, 0.5 mM, $MnCl_2 4H_2O$); iv) metal alloy nanoparticles of zinc iron oxide ($ZnFe_2O_4$) were produced in a medium containing zinc and iron ions (Zn, $ZnSO_4 \cdot 7H_2O$, 0.5 mM, Fe, $Fe(NO_3)_3 \cdot 6H_2O$, 0.5 mM); and v) metal alloy nanoparticles of silver tellurite ($Ag_2TeO_3$) were produced in a medium containing silver (Ag, $AgNO_3$, 0.25, 0.5 mM) and tellurium (Te, $NaTeO_3$, 0.25, 0.5 mM) ions.

Therefore, in a second aspect, the present invention is directed to a method for producing metal alloy nanoparticles, comprising the steps of: (a) culturing in a medium a recombinant microorganism having introduced therein a metallothionein-encoding gene and a phytochelatin synthase-encoding gene; (b) adding to the medium of step (a) two or more metal ions selected from the group consisting of zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), yttrium (Y), aluminum (Al), and europium (Eu), followed by additional culturing, thereby producing metal alloy nanoparticles; and (c) recovering the produced metal alloy nanoparticles.

In the present invention, the added metal ions may be two or more metal ions selected from the group consisting of zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), yttrium (Y), aluminum (Al), and europium (Eu), but is not limited thereto.

In the present invention, it was found that the metal alloy nanoparticles produced by the above-described method consist of zinc manganese oxide ($ZnMn_2O_4$), zinc iron oxide ($ZnFe_2O_4$), nickel iron oxide ($NiFe_2O_4$), cobalt iron oxide ($CoFe_2O_4$), cadmium selenide (CdSe), cadmium zinc (CdZn), cadmium telluride (CdTe), zinc selenide (SeZn), cadmium selenide zinc (CdSeZn), strontium gadolinium (SrGd), praseodymium gadolinium (PrGd), cadmium cesium CdCs), cobalt iron (FeCo), iron cobalt nickel compound (FeCoNi), and silver tellurite ($Ag_2TeO_3$).

In the present invention, it could be found that the surface functional groups of the metal alloy nanoparticles comprise 3300-3000 $cm^{-1}$ (O—H), 2960-2850 $cm^{-1}$ (C—H), 1650-1660 $cm^{-1}$ (amide I), 1540-1535 $cm^{-1}$ (amide II), 1240-1234 $cm^{-1}$ (amide III), and 1150-1030 $cm^{-1}$ (C=O) in an IR spectrum range of 400 to 4000 $cm^{-1}$.

It could be seen that, among the metal nanoparticles synthesized by the above-described method, cobalt iron oxide ($CoFe_2O_4$) nanoparticles are ferromagnetic, and nickel iron oxide ($NiFe_2O_4$), zinc manganese oxide ($ZnMn_2O_4$) and zinc iron oxide ($ZnFe_2O_4$) nanoparticles are paramagnetic.

In particular, in the second aspect, it could be seen that when silver (Ag) and tellurium (Te) are added simultaneously, silver tellurite ($Ag_2TeO_3$) nanoparticles were synthetized, and the surface functional groups of the silver tellurite ($Ag_2TeO_3$) metal alloy nanoparticles comprise 3300-3000 $cm^{-1}$ (O—H), 2960-2850 $cm^{-1}$ (C—H), 1650-1660 $cm^{-1}$ (amide I), 1540-1535 $cm^{-1}$ (amide II), 1240-1234 $cm^{-1}$ (amide III), and 1150-1030 $cm^{-1}$ (C=O).

Therefore, in a third aspect, the present invention is directed to the novel use of silver tellurite ($Ag_2TeO_3$) nanoparticles synthesized using a recombinant microorganism co-expressing metallothionein and phytochelatin synthase.

The silver tellurite ($Ag_2TeO_3$) nanoparticles are diamagnetic, and thus can be used as a contrast agent, wherein the contrast agent may be used for imaging selected from the group consisting of optical imaging, magnetic resonance imaging, precision nuclear medicine imaging, and ultrasound imaging, but is not limited thereto.

Furthermore, the silver tellurite ($Ag_2TeO_3$) nanoparticles show different CV curves depending on scan rate, and have electrochemical characteristics showing peaks at about 0.30 V and 0.40 V in an anode and peaks at −0.50 V and −0.20 V in a cathode. Thus, the silver tellurite ($Ag_2TeO_3$) nanoparticles may be used as a component of an electrode, wherein the electrode may be used in a cell selected from the group consisting of lithium ion cells, fuel cells, solar cells, hydrogen cells, and secondary cells, but is not limited thereto. For example, the metal nanoparticles according to the present invention may be used in an anode for a lithium-ion cell, particularly, a lithium-ion secondary cell. In addition, the metal nanoparticles according to the present invention may be used in an anode for a lithium-ion cell, particularly a lithium-ion secondary cell, which comprises an electrically active material.

The silver tellurite ($Ag_2TeO_3$) nanoparticles according to the present invention may be used as a component of a biosensor and for a semiconductor device.

In addition, the metal nanoparticles synthesized according to the present invention may be used in various applications based on their characteristics or activity. Examples of applications in which the metal nanoparticles according to the present invention can be used include, but are not limited to, electrode activation, a catalyst for glucose oxidation, a catalyst for carbon monoxide oxidation, a catalyst for carbon compound oxidation, a catalyst for synthesis of pyrano[2,3-d] pyrimidines, a catalyst for cobalt compound synthesis, a catalyst for iron compound synthesis, a composition for a storage battery, a composition for a battery, a composition for a lithium secondary cell, a photoelectronic device, a semiconductor device, a light-emitting diode, a self-cooling device, a carrier for drug delivery, a radiotherapy enhancer, an MRI contrast agent, a composition for medical diagnosis, a composition for high-density magnetic recording medium, a composition for electromagnetic wave absorption, an antibacterial composition, a composition for treatment/prevention of oral diseases, a composition for IR detection, a composition for X-ray detection, a composition for gamma-ray detection, a magnetic refrigerant composition, a raw material for a permanent magnet, a biosensor, a composition for graphene tubes, a food additive composition, a tobacco filter composition, a paint pigment composition, a paint drying composition, a porcelain colorant composition, and the like.

In addition, the metal nanoparticles according to the present invention may be used in any fields in which the development and proliferation of microorganisms must be suppressed. Specifically, the metal nanoparticles are advantageously used in medical devices, hand rails, door handles, mobile phones, keyboards, etc. Furthermore, the metal nanoparticles according to the present invention are useful for the disinfection and general antimicrobial treatment, such as deodorizing, of the skin, mucous membrane and hair, preferably for the disinfection of hands and wounds, and may be utilized as an antimicrobial agent in various product forms or compositions for personal and household care use or for industrial and hospital applications including, but not limited to, cosmetic compositions for skin and hair care, for example, lotions; creams; oils; gels; powders; wipes; deodorants like sprays, sticks and roll-ons; cleansers like shower gels; bath additives; liquid and solid soaps (based on synthetic surfactants and salts of saturated and/or unsaturated fatty acids); aqueous and/or alcoholic solutions, e.g., cleansing solutions for the skin; moist cleaning cloths; hand sanitizers; shampoos; rinses; etc.; oral hygiene compositions, for example, in the form of a gel, a paste, a cream or an aqueous preparation (mouthwash); hard surface cleaners, e.g., disinfectant sprays, liquids, or powders; dish or laundry detergents (liquid or solid), floor waxes, glass cleaners, etc.; and industrial and hospital applications (e.g., sterilization of instruments, medical devices, gloves; contact lenses, contact lens cases, contact lens storage solutions, contact lens cleaning solutions).

In another example of the present invention, it was found that the recombinant microorganism was additionally cultured for 12 hours in the medium supplemented with sulfur (S, $Na_2S$, 1 mM) together with silver (Ag, $AgNO_3$, 0.5 mM), indium (In, $InCl_2 4H_2O$, 0.5 mM)), manganese (Mn, $MnSO_4 5H_2O$, 0.5 mM) or tin (Sn, $SnCl_2 4H_2O$, 0.5 mM), and as a result, it was shown that silver sulfide, indium sulfide, manganese sulfide or tin sulfide nanoparticles were produced.

Therefore, in a fourth aspect, the present invention is directed to a method for producing metal sulfide nanoparticles, comprising the steps of: (a) culturing in a medium a recombinant microorganism having introduced therein a metallothionein-encoding gene and a phytochelatin synthase-encoding gene; (b) adding to the medium of step (a) a metal ion selected from the group consisting of i) zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), and europium (Eu); and ii) sulfur, followed by additional culturing, thereby producing metal sulfide nanoparticles; and (c) recovering the produced metal sulfide nanoparticles.

In the present invention, the added metal ion may be selected from the group consisting of zinc (Zn), selenium (Se), tellurium (Te), cesium (Cs), copper (Cu), lead (Pb), nickel (Ni), manganese (Mn), mercury (Hg), cobalt (Co), chromium (Cr), cadmium (Cd), strontium (Sr), iron (Fe), gold (Au), silver (Ag), praseodymium (Pr), gadolinium (Gd), barium (Ba), zirconium (Zr), molybdenum (Mo), indium (In), tin (Sn), lanthanum (La), cerium (Ce), neodymium (Nd), samarium (Sm), and europium (Eu), but is not limited thereto.

In the present invention, the produced metal sulfide nanoparticles may be selected from the group consisting of silver sulfide ($Ag_2S$), indium sulfide (InS), manganese sulfide (MnS), zinc sulfide (ZnS), copper sulfide (CuS), cadmium sulfide (CdS), gold sulfide (AuS), nickel sulfide (NiS), cobalt sulfide (CoS), mercury sulfide (HgS), and tin sulfide (SnS), but is not limited thereto.

In the present invention, it could be found that the surface functional groups of the metal sulfide nanoparticles comprise 3300-3000 cm$^{-1}$ (O—H), 2960-2850 cm$^{-1}$ (C—H), 1650-1660 cm$^{-1}$ (amide I), 1540-1535 cm$^{-1}$ (amide II), 1240-1234 cm$^{-1}$ (amide III), and 1150-1030 cm$^{-1}$ (C=O) in an IR spectrum range of 400 to 4000 cm$^{-1}$.

In the first, second, and fourth aspects of the present invention, the microorganism may be selected from the group consisting of bacteria, yeasts, algae, archaea, and fungi, but is not limited thereto.

In the first, second, and fourth aspects of the present invention, the metallothionein-encoding gene may be represented by SEQ ID NO: 1, and the phytochelatin synthase-encoding gene is represented by SEQ ID NO: 2, but they are not limited thereto.

In the present invention, metal nanoparticles produced in the recombinant microorganism can be recovered by disrupting the microorganism, removing the cell debris by filtration, and collecting the metal nanoparticles from the filtered solution. In one embodiment, the metal nanoparticles can be recovered by centrifuging the microbial culture at 3500 rpm and 4° C. for 15 minutes, removing the supernatant, collecting the microbial pellet, washing the collected microbial pellet three times with PBS buffer, disrupting the cell suspension with a sonicator (VCX-600, Sonics and Materials Inc., USA) equipped with an ultrasonic probe (40 T, Sonics and Materials Inc., USA) (on for 3 sec and off for 3 sec), removing the cell debris by filtration through a 8-µm pore size cellulose filter and then through a 0.1-µm pore size membrane filter (Whatman), and collecting the nanoparticles from the filtered solution. In addition to this method, any method known in the art may also be used to recover the nanoparticles from the microbial cells or the cell culture medium.

In examples of the present invention, a specific medium and culture method has been illustrated, but it will be obvious to a person of ordinary skill in the art that other media can be used as reported in literatures. In examples of the present invention, *E. coli* was used as a microorganism, it will be obvious to those skilled in the art that other bacteria, yeasts and fungi could be used. In addition, although the following examples have illustrated only a specific strain-derived gene as a gene to be introduced, it will be obvious to those skilled in the art that any gene can be used as the gene to be introduced without limitations, as long as it is expressed in a host cell being introduced to show the same activity as that of the above gene.

In the present invention, the concentration of metal ions may be 5 mM to 0.01 mM, preferably 3 mM to 0.1 mM, more preferably 2 to 0.5 mM. If the concentration of metal ions is more than 5 mM, their toxicity to cells may increase to inhibit the growth of the cells, as reported in the literatures (Xiu Z M et al., *Nano Lett.*, 12(8): 4271-4275, 2012; Nies D H, Appl *Microbiol Biotechnol*, 51(6):730-750, 1999). Meanwhile, the size of metal nanoparticles can be controlled by controlling the concentration of metal ions.

In the present invention, an aqueous metal compound can be used as a metal element. For example, an aqueous metal salt, an aqueous metal oxide salt, or a combination thereof can be used.

As used herein, the term "plasmid" means a DNA construct containing a DNA sequence operably linked to a suitable control sequence capable of effecting the expression of the DNA in a suitable host. The plasmid may be a vector, a phage particle, or simply a potential genomic insert. Once incorporated into a suitable host, the plasmid may replicate and function independently of the host genome, or may in some instances, integrate into the genome itself. In the present specification, "plasmid" and "vector" are sometimes used interchangeably, as the plasmid is the most commonly used form of vector. However, the present invention is intended to include other types of vectors with the same function as that would be known or known in the art.

As used herein, the term "recombinant microorganism" refers to a microorganism produced by modifying a part of a gene for a specific purpose, such as introducing a useful gene of any organism into another microorganism by using a genetic recombination technique, deleting a part of a gene of a host microorganism, or adjusting an expression amount. It will be apparent to those skilled in the art that the term can be replaced with the term "genetically modified microorganism", "recombinant strain" or the like. The microorganism may include algae, bacteria, protozoa, fungi, yeast and the like. The microorganism can be preferably selected from the group consisting of bacteria, yeast, and fungi. More preferably, *E. coli* can be selected.

As used herein, the term "crystalline" means a state in which a certain solid forms a crystal in a repetitive atomic arrangement state.

As used herein, the term "amorphous" means an amorphous state, i.e., a state in which a certain solid does not form a crystal in a repetitive atomic arrangement state.

As used herein, the term "nanoparticle" means a particle having a diameter of a nanometer unit.

EXAMPLES

Hereinafter, the present invention will be described in further detail with reference to examples. It will be obvious to a person having ordinary skill in the art that these examples are for illustrative purposes only and are not to be construed to limit the scope of the present invention. Thus, the substantial scope of the present invention will be defined by the appended claims and equivalents thereof.

Example 1: Construction of Expression Vector Co-Expressing Two Heavy Metal-Adsorbing Proteins (Metallothionein and Phytochelatin Synthase)

1-1: Construction of Metallothionein Expression Vector

Using the genomic DNA of *Pseudomonas putida* KT2440 as a template, polymerase chain reaction (PCR) was performed using primers of SEQ ID NOs: 3 and 4, thereby constructing an metallothionein (MT) gene fragment encoding the nucleotide sequence of metallothionein (MT).

```
SEQ ID NO: 3:
5'-ATAGAATTCATGAACGATCACCACCACCACAAC-3'

SEQ ID NO: 4:
5'-TATCTGCAGTTAGGGCGAGATCGGATCACTC-3'
```

Next, the constructed metallothionein fragment was subjected to agarose gel electrophoresis to isolate a 243-bp metallothionein gene fragment which was then digested with two restriction enzymes (EcoRI and PstI). Meanwhile, a pTac15K plasmid which is inducible and containing tac promoter was digested with two restriction enzymes (EcoRI and PstI), and then mixed and ligated with the MT fragment by T4 DNA ligase. The ligation product was transformed into *E. coli* DH5a by a heat shock method. The transformed strain was selected on LB medium containing kanamycin antibiotic (100 g/L), and a pYJ-MT recombinant plasmid was constructed therefrom (FIG. 1).

1-2: Construction of Phytochelatin Synthase Expression Vector

In order to obtain phytochelatin synthase (PCS) from *Arabidopsis thalinana*, a phytochelatin synthase gene fragment encoding the nucleotide sequence of phytochelatin synthase was constructed by PCR using the complementary DNA (cDNA) of *Arabidopsis thalinana* as a template. The PCR was performed using primers of SEQ ID NOs: 5 and 6.

```
SEQ ID NO: 5:
5'-ATAGAATTCATGGCTATGGCGAGTTTATATCGG-3'

SEQ ID NO: 6:
5'-TATGCATGCTTAATAGGCAGGAGCAGCGAGATC-3'
```

Figure 2:
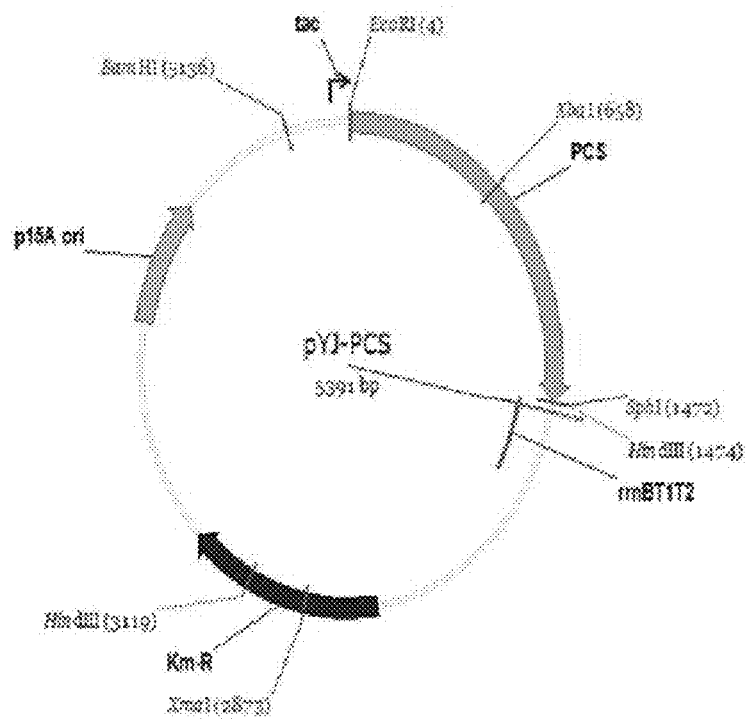
FIG. 2 is a genetic map of the expression vector pYJ-PCS according to the present invention.

Next, the constructed phytochelatin synthase fragment was subjected to agarose gel electrophoresis to isolate a 1458-bp phytochelatin synthase gene fragment which was then digested with two restriction enzymes (EcoRI and SphI). Meanwhile, a pTac15K plasmid which is inducible and containing tac promoter was digested with two restriction enzymes (EcoRI and SphI), and then mixed and ligated with the phytochelatin synthase fragment by T4 DNA ligase. The ligation product was transformed into *E. coli* DH5a by a heat shock method. The transformed strain was selected on LB plate medium containing kanamycin antibiotic (100 g/L), and a pYJ-PCS recombinant plasmid was constructed therefrom (FIG. 2).

1-3: Construction of Vector Co-Expressing Metallothionein and Phytochelatin Synthase In order to construct a vector co-expressing metallothionein and phytochelatin synthase, pYJ-MT-PCS was constructed from the pYJ-MT and pYJ-PCS plasmids constructed as described above. Specifically, the pYJ-PCS vector was subjected to polymerase chain reaction (PCR) using primers of SEQ ID NOs: 7 and 8.

```
SEQ ID NO: 7:
5'-ATACTGCAGTTGACAATTAATCATCGGCTCGTATA-3'

SEQ ID NO: 8:
5'-TATGCATGCTTAATAGGCAGGAGCAGCGAGA-3'
```

Figure 3:
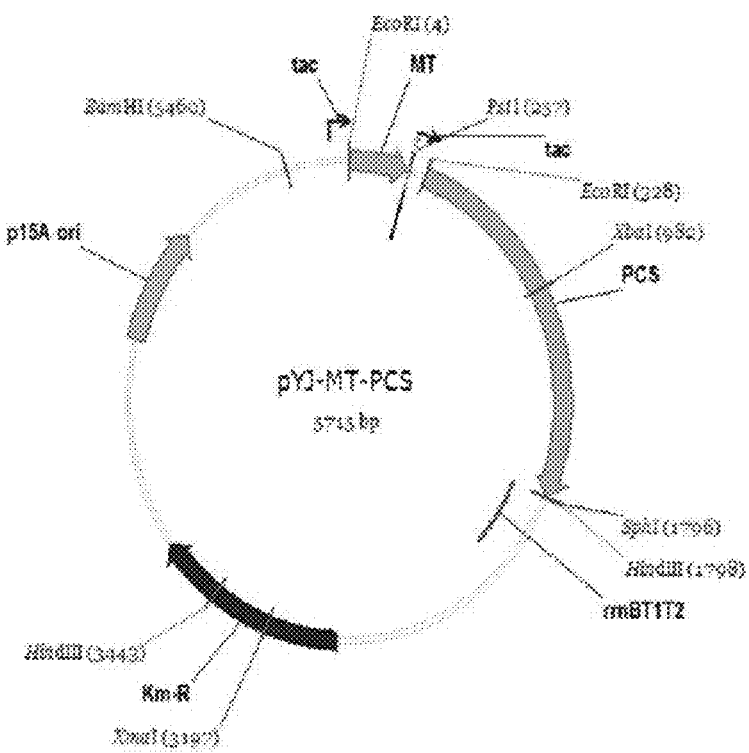
FIG. 3 is a genetic map of the expression vector pYJ-MT-PCS according to the present invention.

Then, a 1545-bp pYJ-PCS gene fragment was isolated from the PCR fragment by agarose gel electrophoresis. Meanwhile, the pYJ-MT plasmid was digested with two restriction enzymes (PstI and SphI), and then mixed and ligated with the pYJ-PCS fragment by T4 DNA ligase. The ligation product was transformed into *E. coli* DH5a by a heat shock method. The transformed strain was selected on LB plate medium containing kanamycin antibiotic (100 g/L), and a pYJ-MT-PCS recombinant plasmid was constructed therefrom (FIG. 3).

1-4: Production of Transformed Recombinant Microorganism and Induction of Expression of Heavy Metal-Adsorbing Proteins The recombinant plasmid pYJ-MT-PCS constructed in Example 1-3 so as to co-express metallothionein and phytochelatin synthase was introduced into *E. coli* DH5a. The transformed recombinant *E. coli* strain was inoculated into a 250 mL flask containing 100 mL of LB liquid medium and was cultured at 37° C. When the *E. coli* strain reached an optical density (OD) of 0.6 at a wavelength of 600 nm, IPTG (isopropyl-D-1-thiogalactopyranoside) was added to the medium to induce expression of metallothionein and phytochelatin synthase. The tac promoter inserted in the pYJ-MT-PCS was inducible by IPTG, and IPTG was added to the medium to a final concentration of 1 mM to induce the expression.

Example 2: Synthesis of Single-Element Metal Nanoparticles Using Recombinant Microorganism and Characterization Thereof 2-1: Synthesis of Single-Element Metal Nanoparticles Using Recombinant Microorganism One hour after inducing expression of metallothionein and phytochelatin synthase in the recombinant microorganism produced in Example 1 above by IPTG, barium (Ba, $(CH_3COO)_2Ba$, 0.5 mM), zirconium (Zr, $K_2ZrF_6$, 0.5 mM), molybdenum (Mo, $Na_2MoO_4 2H_2O$, 0.5 mM), indium (In, $InCl_2 4H_2O$, 0.5 mM), tin (Sn, $SnCl_2 4H_2O$, 0.5 mM), lanthanum (La, $La(NO_3)_3 6H_2O$, 0.5 mM), cerium (Ce, $Ce(NO_3)_3 6H_2O$, 0.5 mM) or praseodymium (Pr, $Pr(NO_3)_3 6H_2O$, 0.5 mM) was added to the LB liquid medium (Tryptone 10 g/L, yeast extract 5 g/L, NaCl 5 g/L, pH 6.5) in which the recombinant *E. coli* strain has been cultured, after which the recombinant microorganism was additionally cultured for 12 hours. The culture was centrifuged at 3500 rpm and 4° C. for 15 minutes, after which the supernatant was discarded and the *E. coli* pellet was collected. The *E. coli* pellet was washed three times with PBS buffer, and then dried in a freeze-dryer under vacuum for one day or more. Synthesis of nanoparticles was examined using transmission electron microscopy (TEM) (Tecnai F20, Philips, Netherlands) and energy-dispersive X-ray spectroscopy (EDX) HD/MAX-2,500, Rigaku, Japan) with CuKa radiation ($\lambda$=1.5406 Å)).

Figure 4:
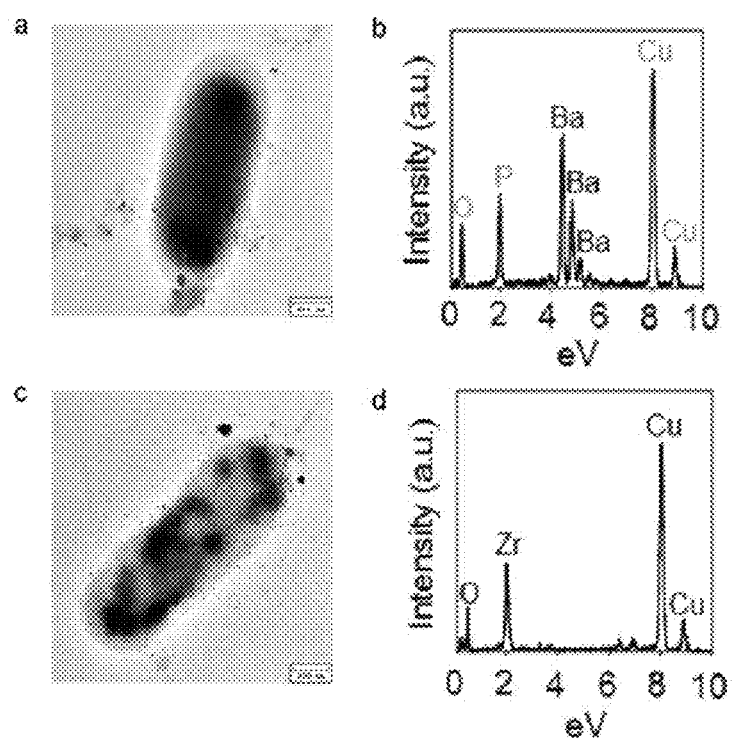
FIG. 4 shows electron micrographs and X-ray spectroscopy graphs of amorphous nanoparticles of barium (Ba) and zirconium (Zr) [(a and b) barium; (c and d) zirconium; (a and c) electron micrographs; (b and d) X-ray spectroscopy graphs].
Figure 5:
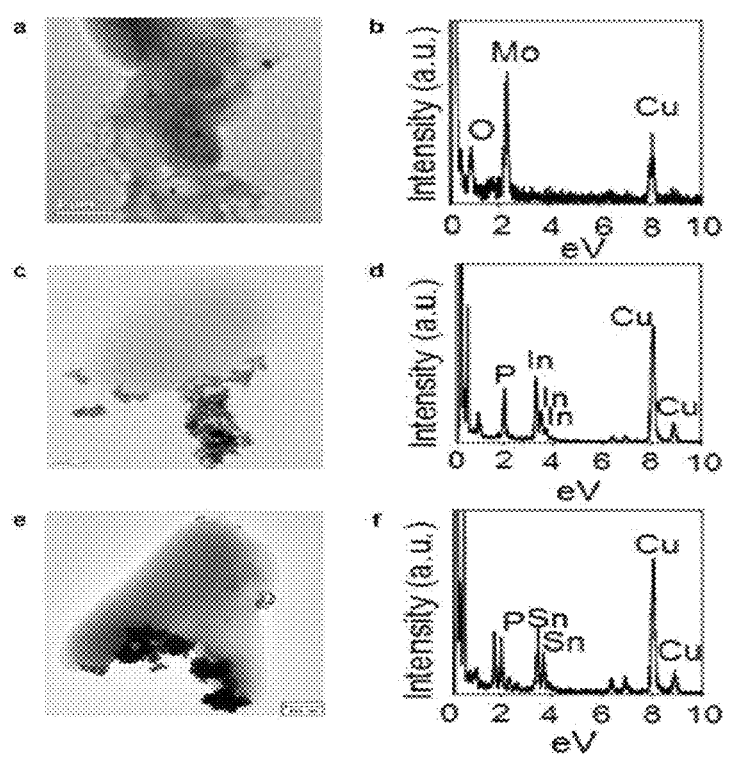
FIG. 5 shows electron micrographs and X-ray spectroscopy graphs of crystalline nanoparticles of molybdenum (Mo), indium (In) and tin (Sn), which are transition elements [(a and b) molybdenum; (c and d) indium; (e and f) tin; (a, c and e) electron micrographs; (b, d and f) X-ray spectroscopy graphs].
Figure 6:
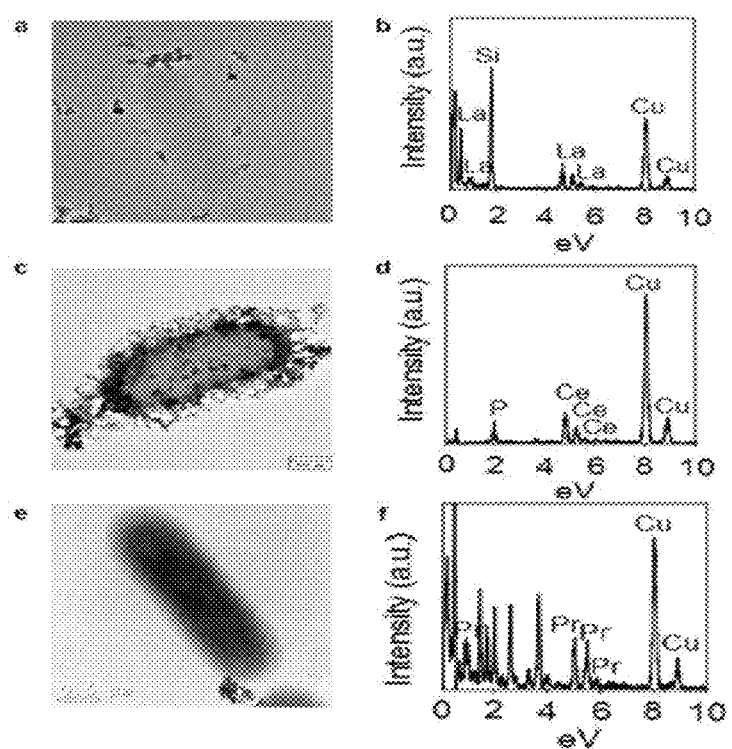
FIG. 6 shows electron micrographs and X-ray spectroscopy graphs of amorphous nanoparticles of lanthanum (La), cerium (Ce) and praseodymium (Pr), which are lanthanides [(a and b) lanthanum; (c and d) cerium; (e and f) praseodymium; (a, c and e) electron micrographs; (b, d and f) X-ray spectroscopy graphs].

As a result, as can be seen in FIGS. 4 to 6, amorphous metal nanoparticles corresponding to each of the metal elements were synthesized.

2-2: Analysis of Surface Functional Groups of Single-Element Metal Nanoparticles Synthesized Using Recombinant Microorganism In order to confirm the surface functional groups of the single-element metal nanoparticles synthesized in Example 2-1 above, the synthesized single-element metal nanoparticles were analyzed using a Fourier transform infrared spectrophotometer (FT-IR) (Nicolet™ iS™50, Thermo Scientific, USA) in a range from 400 to 4000 cm$^{-1}$ at room temperature.

Figure 7:
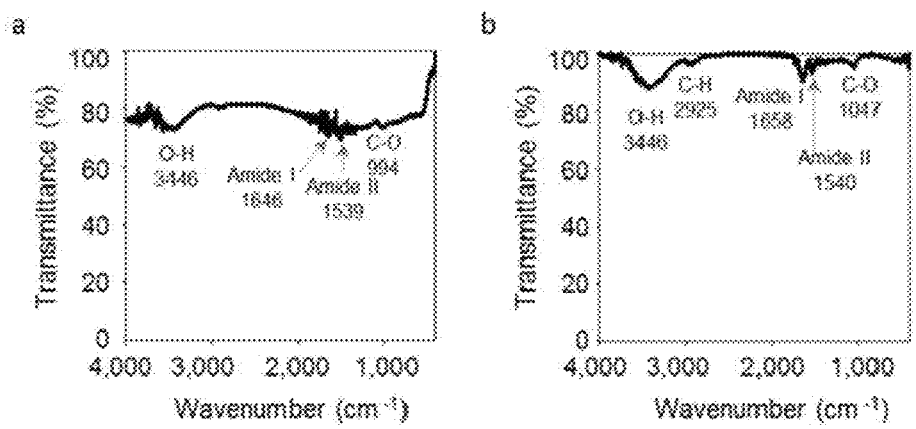
FIG. 7 shows the FT-IR spectra of barium (Ba) and zirconium (Zr) nanoparticles [(a) barium; (b) zirconium].
Figure 8:
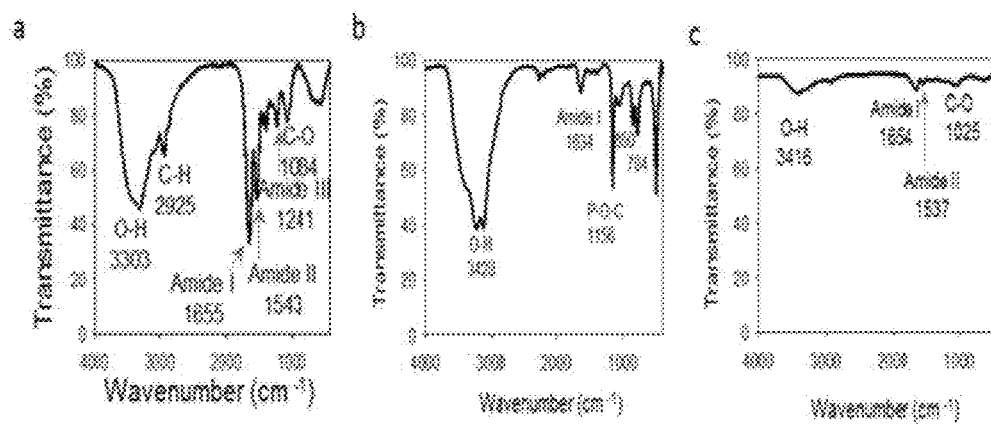
FIG. 8 shows the FT-IR spectra of molybdenum (Mo), indium (In) and tin (Sn) nanoparticles [(a) molybdenum; (b) indium; (c) tin].
Figure 9:
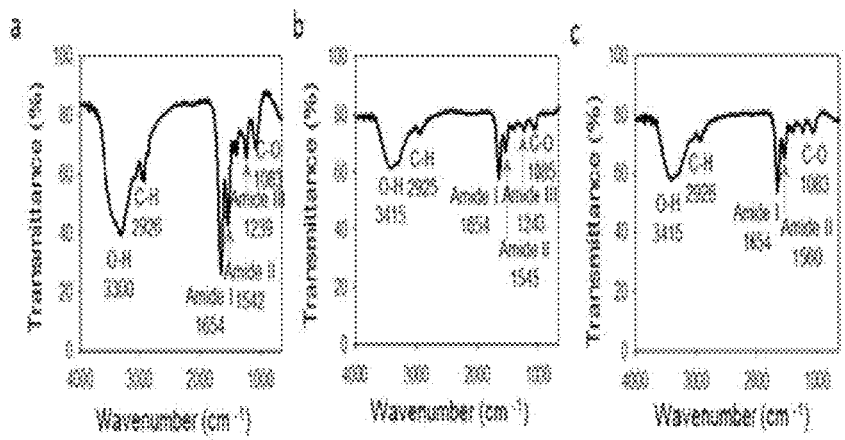
FIG. 9 shows the FT-IR spectra of lanthanum (La), cerium (Ce) and praseodymium (Pr) [(a) lanthanum; (b) cerium; (c) praseodymium].

As a result, as can be seen in FIGS. 7 to 9, the surface functional groups of single-element metal nanoparticles synthesized using recombinant microorganism comprise 3300-3000 cm$^{-1}$ (OH groups), 2960-2850 cm$^{-1}$ (C—H), 1650-1660 cm$^{-1}$ (amide I), 1540-1535 cm$^{-1}$ (amide II), 1240-1234 cm$^{-1}$ (amide III), and 1150-1030 cm$^{-1}$ (C=O).

Example 3: Synthesis of Metal Alloy Nanoparticles Using Recombinant Microorganism and Characterization Thereof 3-1: Synthesis of Metal Alloy Nanoparticles Using Recombinant Microorganism One hour after inducing expression of metallothionein and phytochelatin synthase in the recombinant microorganism produced in Example 1 above by IPTG, i) cobalt and iron (Co, $CoCl_2$, 0.5 mM, Fe, $Fe(NO)_3.6H_2O$, 0.5 mM), ii) nickel and iron (Ni, $NiCl_2.6H_2O$, 0.5 mM, Fe, $Fe(NO)_3.6H_2O$, 0.5 mM), iii) zinc and manganese (Zn, $ZnSO_4.7H_2O$, 0.5 mM, $MnCl_2 4H_2O$), 0.5 mM or iv) zinc and iron (Zn, $ZnSO_4.7H_2O$, 0.5 mM, Fe, $Fe(NO)_3.6H_2O$, 0.5 mM) ions, were added to the LB liquid medium (Tryptone 10 g/L, yeast extract 5 g/L, NaCl 5 g/L' pH 6.5) in which the recombinant *E. coli* strain has been cultured, after which the recombinant microorganism was additionally cultured for 12 hours. The culture was centrifuged at 3500 rpm and 4° C. for 15 minutes, after which the supernatant was discarded and the *E. coli* pellet was collected. The *E. coli* pellet was washed three times with PBS buffer, and then dried in a freeze-dryer under vacuum for one day or more. Synthesis of nanoparticles was examined using transmission electron microscopy (TEM).

Figure 10:
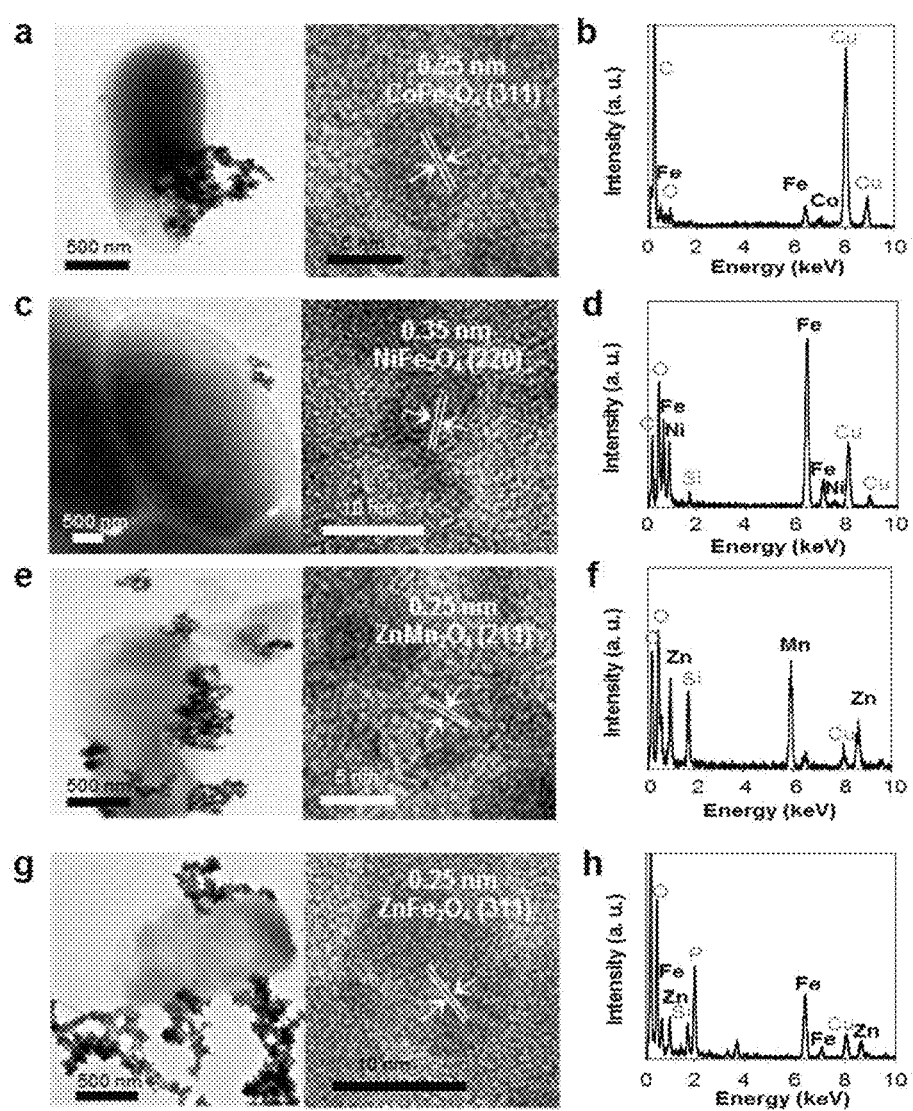
FIG. 10 shows electron micrographs and X-ray spectroscopy graphs of cobalt iron oxide ($CoFe_2O_4$), nickel iron oxide ($NiFe_2O_4$), zinc manganese oxide ($ZnMn_2O_4$) and zinc iron oxide ($ZnFe_2O_4$), which are magnetic crystalline metal nanoparticles synthesized using a recombinant microorganism [(a) an electron micrograph of cobalt iron oxide ($CoFe_2O_4$); (b) an X-ray spectroscopy graph of cobalt iron oxide ($CoFe_2O_4$); (c) an electron micrograph of nickel iron oxide ($NiFe_2O_4$); (d) an X-ray spectroscopy graph of nickel iron oxide ($NiFe_2O_4$); (e) an electron micrograph of zinc manganese oxide ($ZnMn_2O_4$); (f) an X-ray spectroscopy graph of zinc manganese oxide ($ZnMn_2O_4$); (g) an electron micrograph of zinc iron oxide ($ZnFe_2O_4$); (h) an X-ray spectroscopy graph of zinc iron oxide ($ZnFe_2O_4$)].

As a result, as shown in FIG. 10, it could be seen by transmission electron microscopy (TEM) (Tecnai F20, Philips, Netherlands) that i) metal alloy nanoparticles of cobalt iron oxide ($CoFe_2O_4$) were synthesized in the medium supplemented with cobalt and iron; ii) metal alloy nanoparticles of nickel iron oxide ($NiFe_2O_4$) were synthesized in the medium supplemented with nickel and iron; iii) metal alloy nanoparticles of zinc manganese oxide ($ZnMn_2O_4$) were synthesized in the medium supplemented with zinc and manganese; and iv) metal alloy nanoparticles of zinc iron oxide ($ZnFe_2O_4$) were synthesized in the medium supplemented with zinc (Zn, $ZnSO_4 \cdot 7H_2O$, 1 mM) and iron ions.

Figure 11:
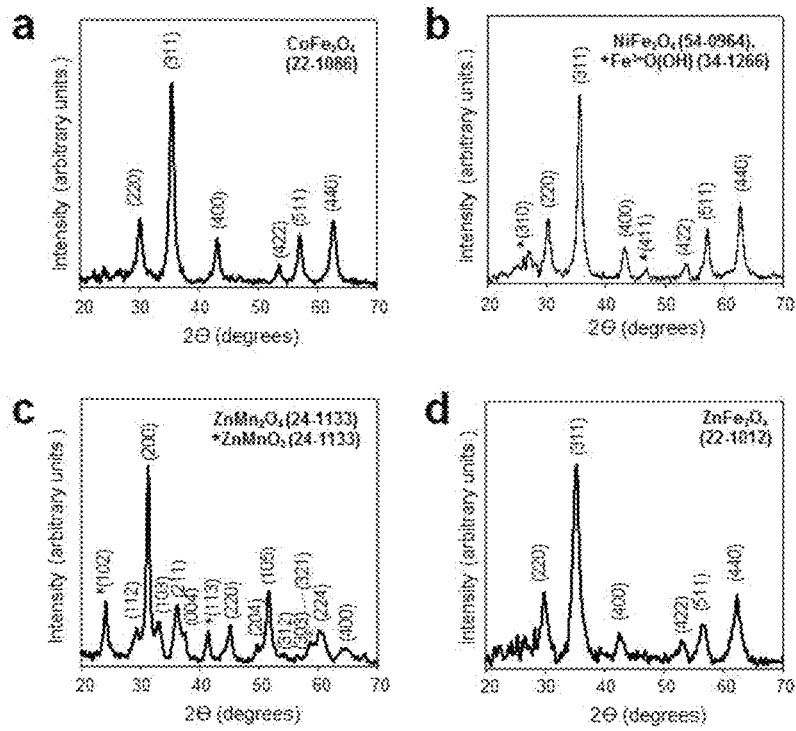
FIG. 11 shows X-ray diffraction graphs of cobalt iron oxide ($CoFe_2O_4$), nickel iron oxide ($NiFe_2O_4$), zinc manganese oxide ($ZnMn_2O_4$) and zinc iron oxide ($ZnFe_2O_4$), which are magnetic crystalline metal nanoparticles synthesized using a recombinant microorganism [(a) an X-ray diffraction graph of cobalt iron oxide ($CoFe_2O_4$); (b) an X-ray diffraction graph of nickel iron oxide ($NiFe_2O_4$); (c) an X-ray diffraction graph of zinc manganese oxide ($ZnMn_2O_4$); (d) an X-ray diffraction graph of zinc iron oxide ($ZnFe_2O_4$)].

Meanwhile, as shown in FIG. 11, the crystal structures of the cobalt iron oxide ($CoFe_2O_4$), nickel iron oxide ($NiFe_2O_4$), zinc manganese oxide ($ZnMn_2O_4$) and zinc iron oxide ($ZnFe_2O_4$) nanoparticles synthesized using the recombinant *E. coli* strain could be confirmed by energy-dispersive X-ray spectroscopy (X-ray Diffraction, XRD) HD/MAX-2,500, Rigaku, Japan) with CuKa radiation ($\lambda$=1.5406 Å)).

3-2: Confirmation of Surface Functional Groups of Synthesized Metal Alloy Nanoparticles In order to confirm the surface functional groups of the metal alloy nanoparticles synthesized in Example 3-1 above, the synthesized metal alloy nanoparticles were analyzed using a Fourier transform infrared spectrophotometer (FT-IR) (Nicolet™ iS™50, Thermo Scientific, USA) in a range from 400 to 4000 $cm^{-1}$ at room temperature.

Figure 12:
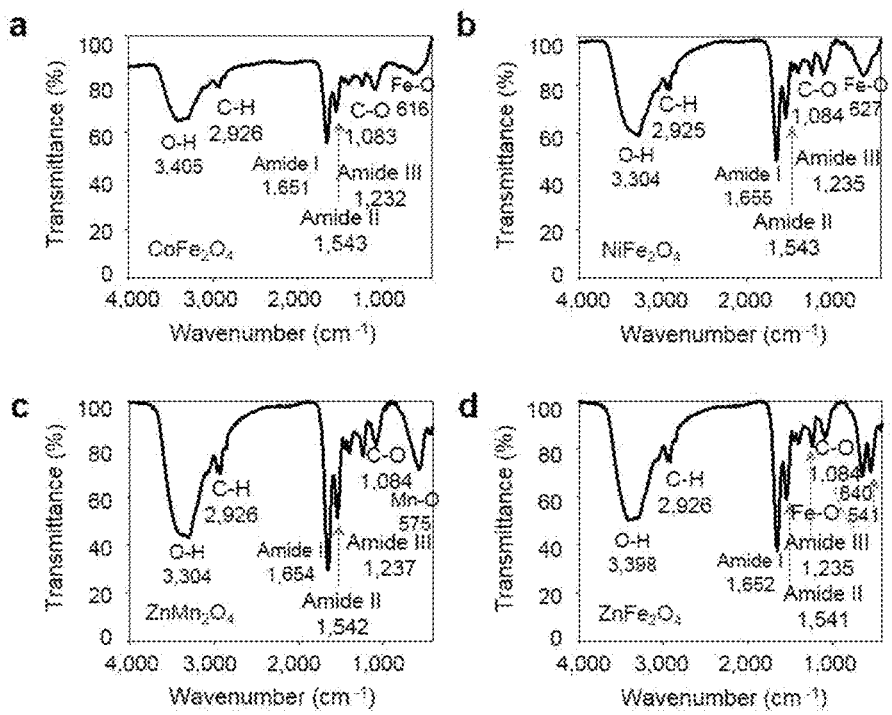
FIG. 12 shows the FT-IR spectra of cobalt iron oxide ($CoFe_2O_4$), nickel iron oxide ($NiFe_2O_4$), zinc manganese oxide ($ZnMn_2O_4$) and zinc iron oxide ($ZnFe_2O_4$), which are magnetic metal nanoparticles synthesized using recombinant microorganisms.

As a result, as can be seen in FIG. 12, it was found that the surface functional groups of metal alloy nanoparticles synthesized using recombinant microorganism comprise 3300-3000 $cm^{-1}$ (O—H), 2960-2850 $cm^{-1}$ (C—H), 1650-1660 $cm^{-1}$ (amide I), 1540-1535 $cm^{-1}$ (amide II), 1240-1234 $cm^{-1}$ (amide III), and 1150-1030 $cm^{-1}$ (C=O).

3-3: Analysis of Magnetic Properties of Synthesized Metal Alloy Nanoparticles

In order to examine the magnetic properties of the nanoparticles produced in Example 3-1, magnetic hysteresis (M-H) curves of the nanoparticles were measured using an MPMS3 (magnetic property measurement system) (SQUID-VSM) (Quantum Design, USA) with SQUID-VSM function. Measurement of the M-H curves was performed at a temperature of 300K and at a magnetic field intensity of −50K Oe to +50K Oe.

Figure 13:
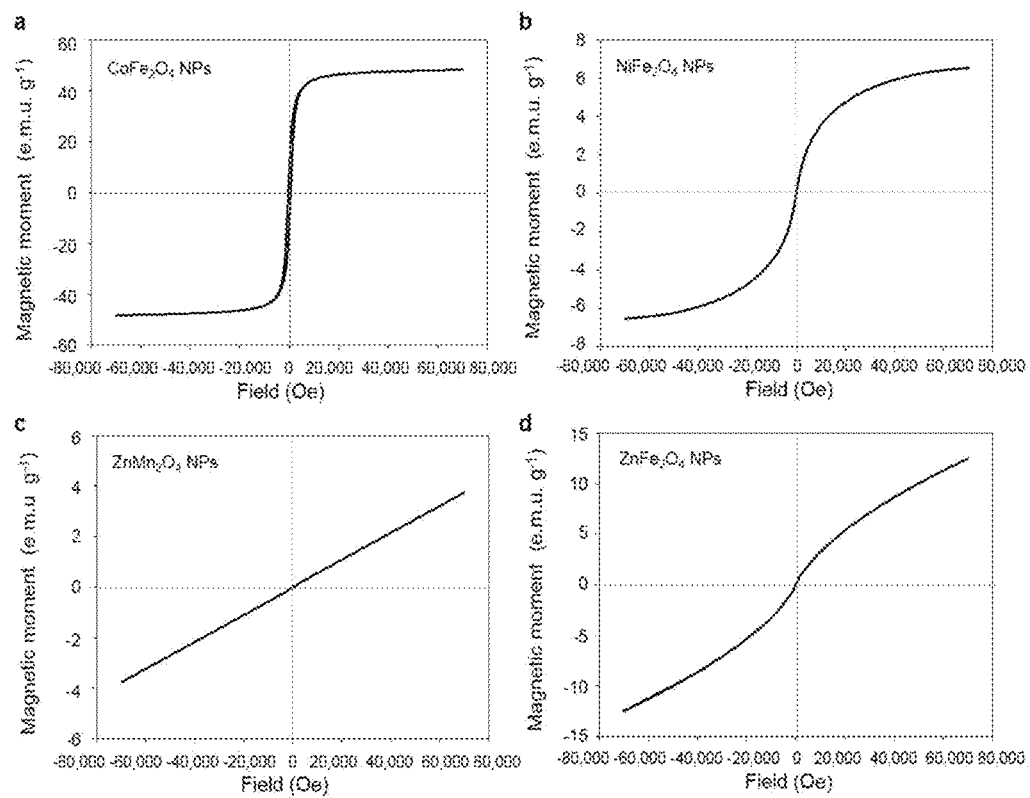
FIG. 13 shows magnetic hysteresis (M-H) curves of cobalt iron oxide ($CoFe_2O_4$), nickel iron oxide ($NiFe_2O_4$), zinc manganese oxide ($ZnMn_2O_4$) and zinc iron oxide ($ZnFe_2O_4$), which are magnetic metal nanoparticles synthesized using a recombinant microorganism [(a) an M-H curve of cobalt iron oxide ($CoFe_2O_4$); (b) an M-H curve of nickel iron oxide ($NiFe_2O_4$); (c) an M-H curve of zinc manganese oxide ($ZnMn_2O_4$); (d) an M-H curve of zinc iron oxide ($ZnFe_2O_4$)].

As a result, as shown in FIG. 13, it could be seen that the cobalt iron oxide ($CoFe_2O_4$) nanoparticles were ferromagnetic, and the nickel iron oxide ($NiFe_2O_4$), zinc manganese oxide ($ZnMn_2O_4$) and zinc iron oxide ($ZnFe_2O_4$) nanoparticles were paramagnetic.

Example 4: Synthesis of Metal Alloy Nanoparticles of Silver Tellurite ($Ag_2TeO_3$) Using Recombinant Microorganism and Characterization Thereof 4-1: Synthesis of Metal Alloy Nanoparticles Using Recombinant Microorganism One hour after inducing expression of metallothionein and phytochelatin synthase in the recombinant microorganism produced in Example 1 above by IPTG, silver (Ag, $AgNO_3$, 0.25, 1 mM) and tellurium (Te, $NaTeO_3$, 0.25, 1 mM) ions were added to the LB liquid medium (Tryptone 10 g/L, yeast extract 5 g/L, NaCl 5 g/L, pH 6.5) in which the recombinant *E. coli* strain has been cultured, after which the recombinant microorganism was additionally cultured for 12 hours. The culture was centrifuged at 3500 rpm and 4° C. for 15 minutes, after which the supernatant was discarded and the *E. coli* pellet was collected. The *E. coli* pellet was washed three times with PBS buffer, and then dried in a freeze-dryer under vacuum for one day or more. Synthesis of nanoparticles was examined using transmission electron microscopy (TEM).

Figure 14:
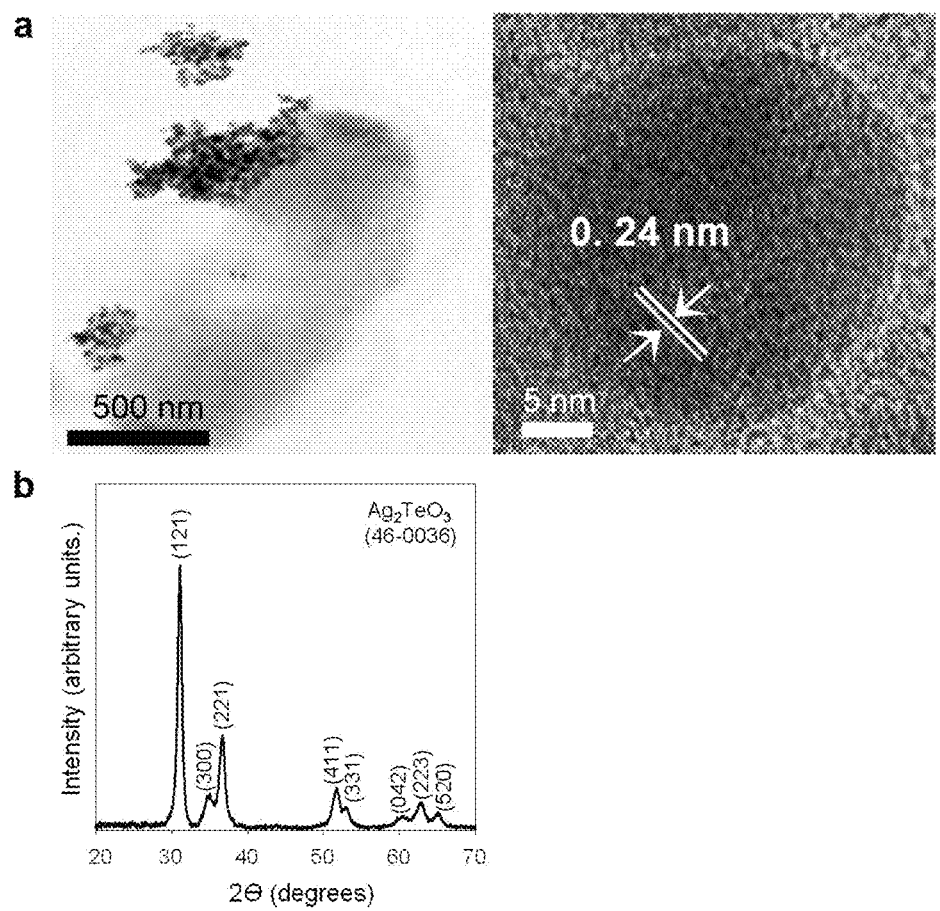
FIG. 14 shows a transmission electron micrograph (a) and X-ray diffraction graph (b) of crystalline nanoparticles of silver tellurite ($Ag_2TeO_3$), produced using a recombinant microorganism.
Figure 15:
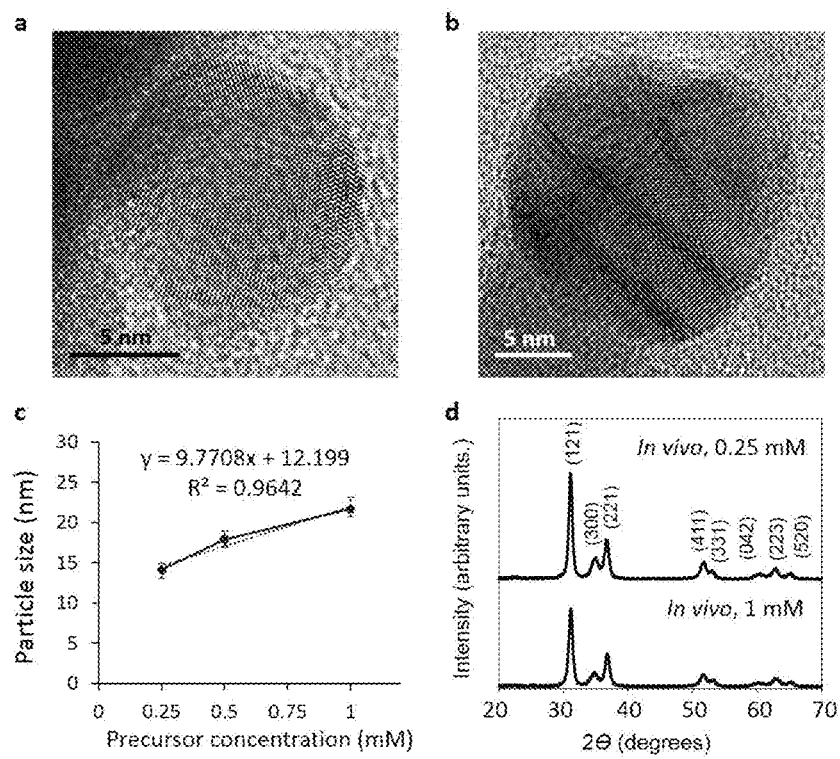
FIG. 15 shows transmission electron micrographs (a) and (b) of silver tellurite ($Ag_2TeO_3$) nanoparticles having various sizes, produced using a recombinant microorganism, a graph (c) showing the correlation between metal ion concentration and the particle size of the nanoparticles, and an X-ray diffraction graph (d) of the nanoparticles.

As a result, as shown in FIGS. 14 and 15, it could be seen by transmission electron microscopy (TEM) (Tecnai F20, Philips, Netherlands) that silver tellurite ($Ag_2TeO_3$) nanoparticles having various sizes were synthesized by the recombinant *E. coli* in the medium supplemented with silver and tellurium, and it could also be seen by energy-dispersive X-ray spectroscopy ((D/MAX-2,500, Rigaku, Japan) with CuKa radiation (A=1.540631)) that the synthesized nanoparticles were silver tellurite ($Ag_2TeO_3$).

4-2: Confirmation of Surface Functional Groups of Synthesized Silver Tellurite ($Ag_2TeO_3$) Nanoparticles In order to confirm the surface functional groups of the silver tellurite ($Ag_2TeO_3$) nanoparticles synthesized in Example 4-1 above, the silver tellurite ($Ag_2TeO_3$) nanoparticles were analyzed using a Fourier transform infrared spectrophotometer (FT-IR) (Nicolet™ iS™50, Thermo Scientific, USA) in a range from 400 to 4000 $cm^{-1}$ at room temperature.

Figure 16:
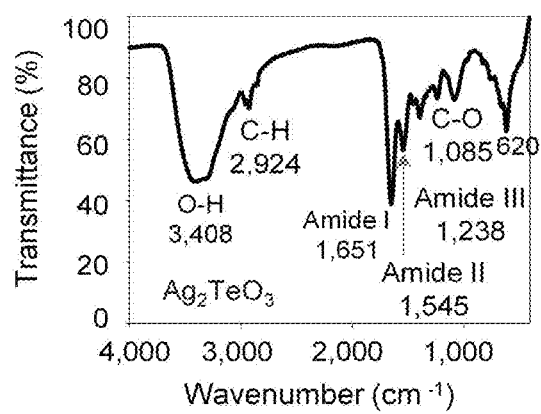
FIG. 16 is an FT-IR graph showing the surface functional groups of silver tellurite ($Ag_2TeO_3$) nanoparticles produced using a recombinant microorganism.

As a result, as can be seen in FIG. 16, it was found that the surface functional groups of silver tellurite ($Ag_2TeO_3$) nanoparticles synthesized using recombinant microorganism comprise 3300-3000 $cm^{-1}$ (O—H), 2960-2850 $cm^{-1}$ (C—H), 1650-1660 $cm^{-1}$ (amide I), 1540-1535 $cm^{-1}$ (amide II), 1240-1234 $cm^{-1}$ (amide III), and 1150-1030 $cm^{-1}$ (C=O).

4-3: Analysis of Magnetic Properties of Synthesized Silver Tellurite ($Ag_2TeO_3$) Nanoparticles In order to examine the magnetic properties of the silver tellurite ($Ag_2TeO_3$) nanoparticles produced in Example 4-1, magnetic hysteresis (M-H) curves of the nanoparticles were measured using an MPMS3 (magnetic property measurement system) (SQUID-VSM) (Quantum Design, USA) with SQUID-VSM function. Measurement of the M-H curves was performed at a temperature of 300K and a magnetic field intensity of −70K Oe to +70K Oe.

Figure 17:
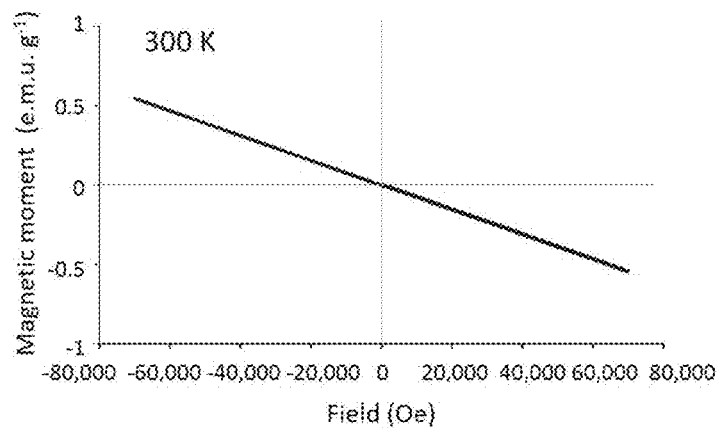
FIG. 17 is a magnetic hysteresis (M-H) curve showing the magnetic properties of silver tellurite ($Ag_2TeO_3$) nanoparticles produced using a recombinant microorganism.

As a result, as can be seen in FIG. 17, it could be found that the synthesized silver tellurite ($Ag_2TeO_3$) nanoparticles are diamagnetic.

4-4: Analysis of Electrochemical Properties of Synthesized Silver Tellurite ($Ag_2TeO_3$) Nanoparticles To analyze the electrochemical properties of the silver tellurite ($Ag_2TeO_3$) nanoparticles produced in Example 4-1, an electrochemical analyzer (Potentiostat; Princeton applied research, VSP) was used. The electrochemical properties of the nanoparticles were measured by cyclic voltammetry (CV) in 1M NaOH aqueous solution. To this end, the produced silver tellurite ($Ag_2TeO_3$) nanoparticles were dried on a glassy carbon electrode to form a working electrode. Furthermore, a platinum (Pt) wire was used as a counter electrode, and silver/silver chloride (Ag/AgCl) was used as a reference electrode. Measurement by cyclic voltammetry (CV) was performed at a voltage ranging from −0.4 to +0.5 V and at different scan rates of 10, 20, 30, 50 and 100 mV/s.

Figure 18:
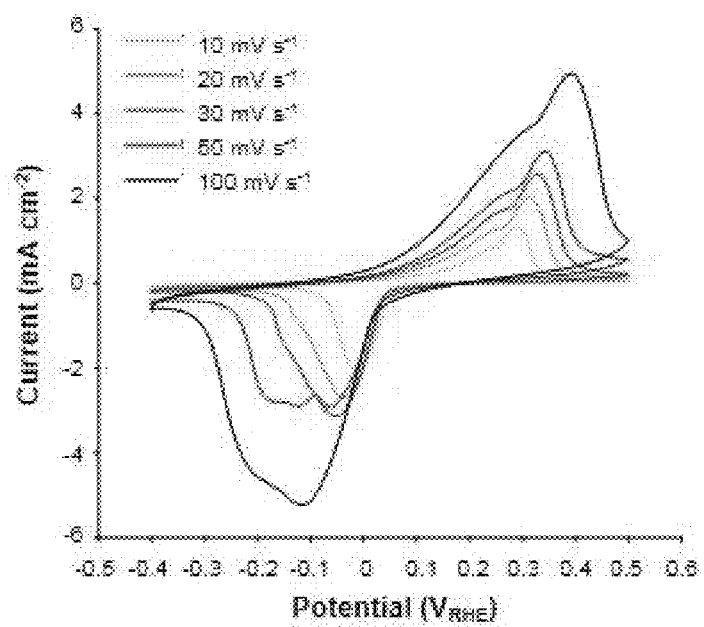
FIG. 18 shows cyclic voltammograms indicating the electrochemical properties of silver tellurite ($Ag_2TeO_3$) nanoparticles produced using a recombinant microorganism.

As a result, as shown in FIG. 18, it could be seen that the silver tellurite ($Ag_2TeO_3$) nanoparticles showed different CV curves depending on scan rate, and had electrochemical properties showing peaks at about 0.30 V and 0.40 V in the anode and peaks at about −0.50 V and −0.20 V in the cathode.

Example 5: Synthesis of Metal Sulfide Nanoparticles Using Recombinant Microorganism and Characterization Thereof 5-1: Synthesis of Metal Sulfide Nanoparticles Using Recombinant Microorganism One hour after inducing expression of metallothionein and phytochelatin synthase in the recombinant microorganism produced in Example 1 above by IPTG, sulfur (S, $Na_2S$, 1 mM) together with silver (Ag, $AgNO_3$, 1 mM), indium (In, $InCl_3 4H_2O$, 1 mM)), manganese (Mn, $MnSO_4 5H_2O$, 1 mM) or tin (Sn, $SnCl_2 4H_2O$, 1 mM) were added to the LB liquid medium (Tryptone 10 g/L, yeast extract 5 g/L, NaCl 5 g/L, pH 6.5) in which the recombinant E. coli strain has been cultured, after which the recombinant microorganism was additionally cultured for 12 hours.

The culture was centrifuged at 3500 rpm and 4° C. for 15 minutes, after which the supernatant was discarded and the E. coli pellet was obtained. The E. coli pellet was washed three times with PBS buffer, and then dried in a freeze-dryer under vacuum for one day or more. Synthesis of nanoparticles was examined using transmission electron microscopy (TEM) (Tecnai F20, Philips, Netherlands) and energy-dispersive X-ray spectroscopy (EDX) HD/MAX-2,500, Rigaku, Japan) with CuKa radiation ($\lambda$=1.5406 Å)).

Figure 19:
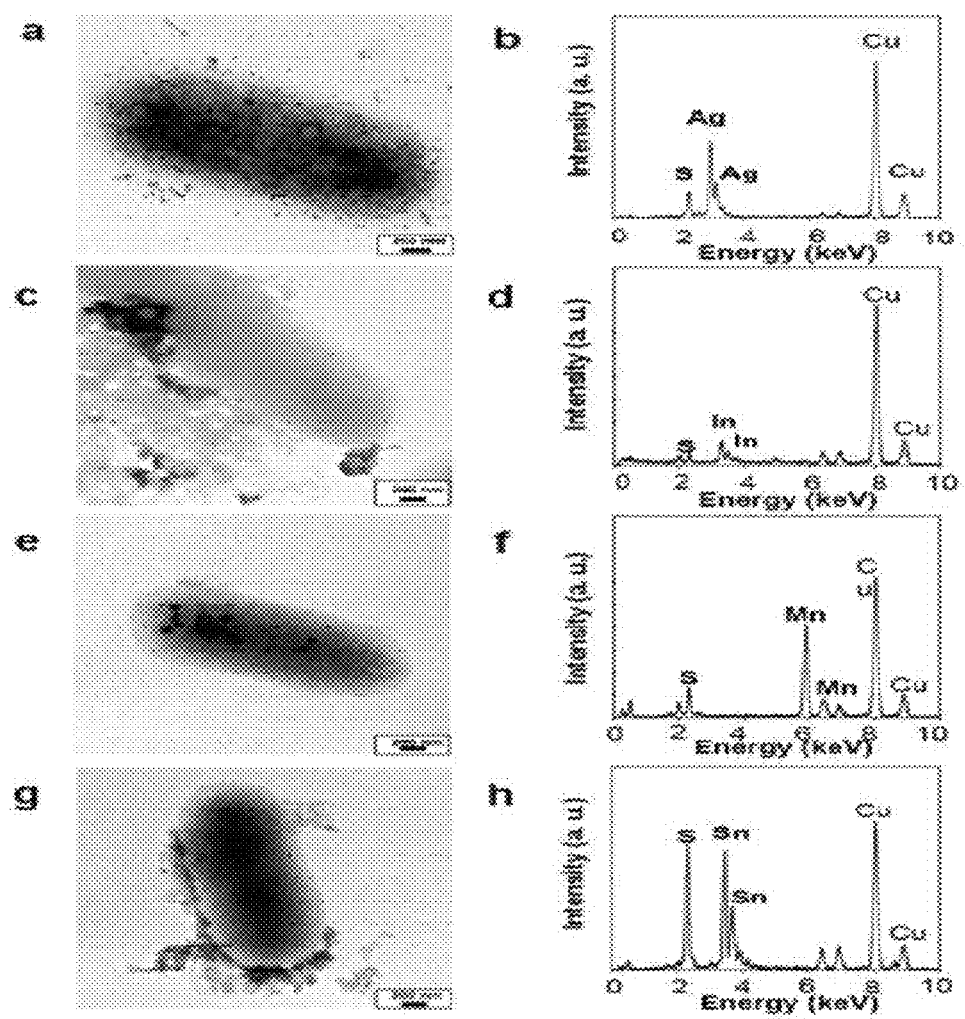
FIG. 19 shows electron micrographs and spectroscopy graphs of crystalline nanoparticles of silver sulfide ($Ag_2S$), indium sulfide (InS), manganese sulfide (MnS) and tine sulfide (SnS), which are metal sulfides [(a and b) silver sulfide; (c and d) indium sulfide; (e and f) manganese sulfide; (g and h) tin sulfide; (a, c, e and g) electron micrographs; (b, d, f and h) spectroscopy graphs].

As a result, as shown in FIG. 19, it could be seen that Synthesis of nanoparticles of silver sulfide ($Ag_2S$), indium sulfide (InS), manganese sulfide (MnS), or tin sulfide (SnS) in the medium to which silver (Ag), indium (In), manganese (Mn) or tin (Sn) and sulfur are added was examined using transmission electron microscopy and energy-dispersive X-ray spectroscopy.

5-2: Confirmation of Surface Functional Groups of Synthesized Metal Sulfide Nanoparticles In order to confirm the surface functional groups of the metal sulfide nanoparticles synthesized in Example 5-1 above, the synthesized metal sulfide nanoparticles were analyzed using a Fourier transform infrared spectrophotometer (FT-IR) (Nicolet™ iS™50, Thermo Scientific, USA) in a range from 400 to 4000 $cm^{-1}$ at room temperature.

Figure 20:
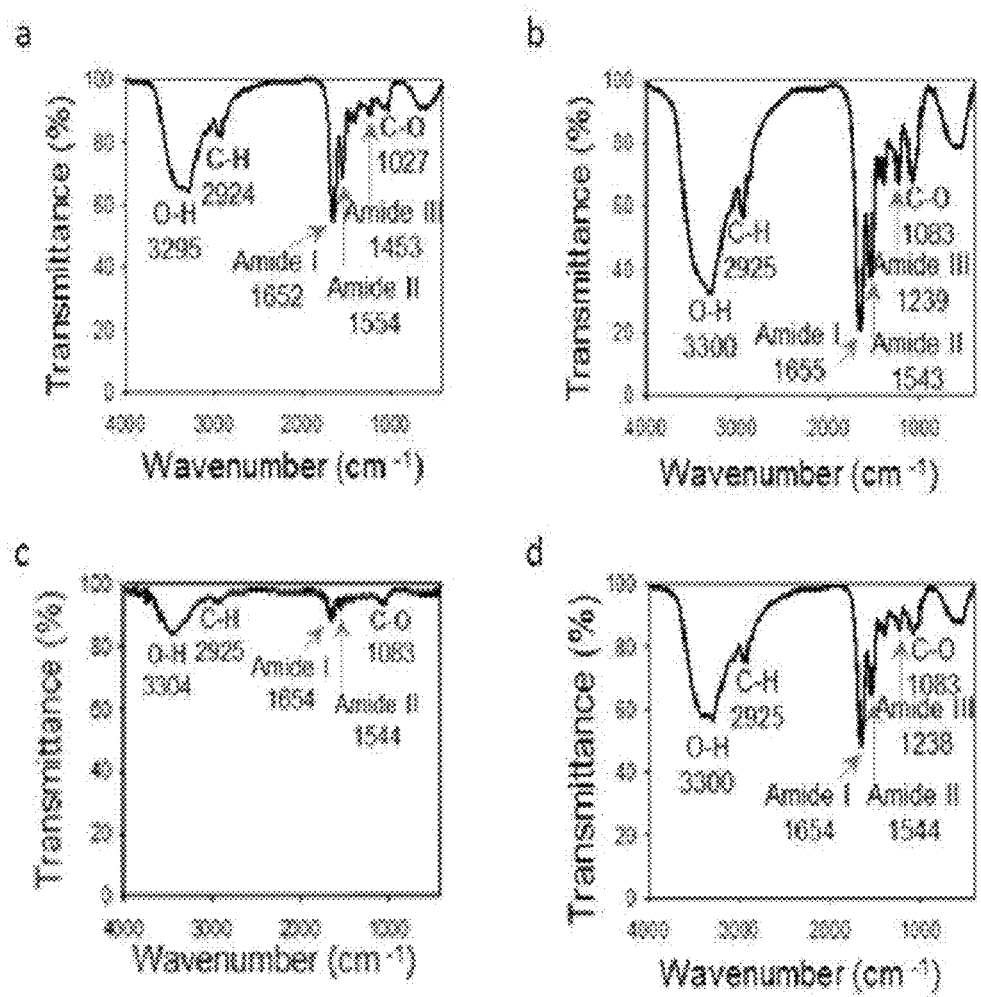
FIG. 20 shows FT-IR spectra indicating the functional groups of silver sulfide ($Ag_2S$), indium sulfide (InS), manganese sulfide (MnS) and tin sulfide (SnS) nanoparticles [(a) silver sulfide; (b) indium sulfide; (c) manganese sulfide; (d) tin sulfide].

As a result, as can be seen in FIG. 20, it was found that the surface functional groups of metal sulfide nanoparticles synthesized through the recombinant microorganism using recombinant microorganism comprise 3300-3000 $cm^{-1}$ (O—H), 2960-2850 $cm^{-1}$ (C—H), 1650-1660 $cm^{-1}$ (amide I), 1540-1535 $cm^{-1}$ (amide II), 1240-1234 $cm^{-1}$ (amide III), and 1150-1030 $cm^{-1}$ (C=O).

Figure 21:
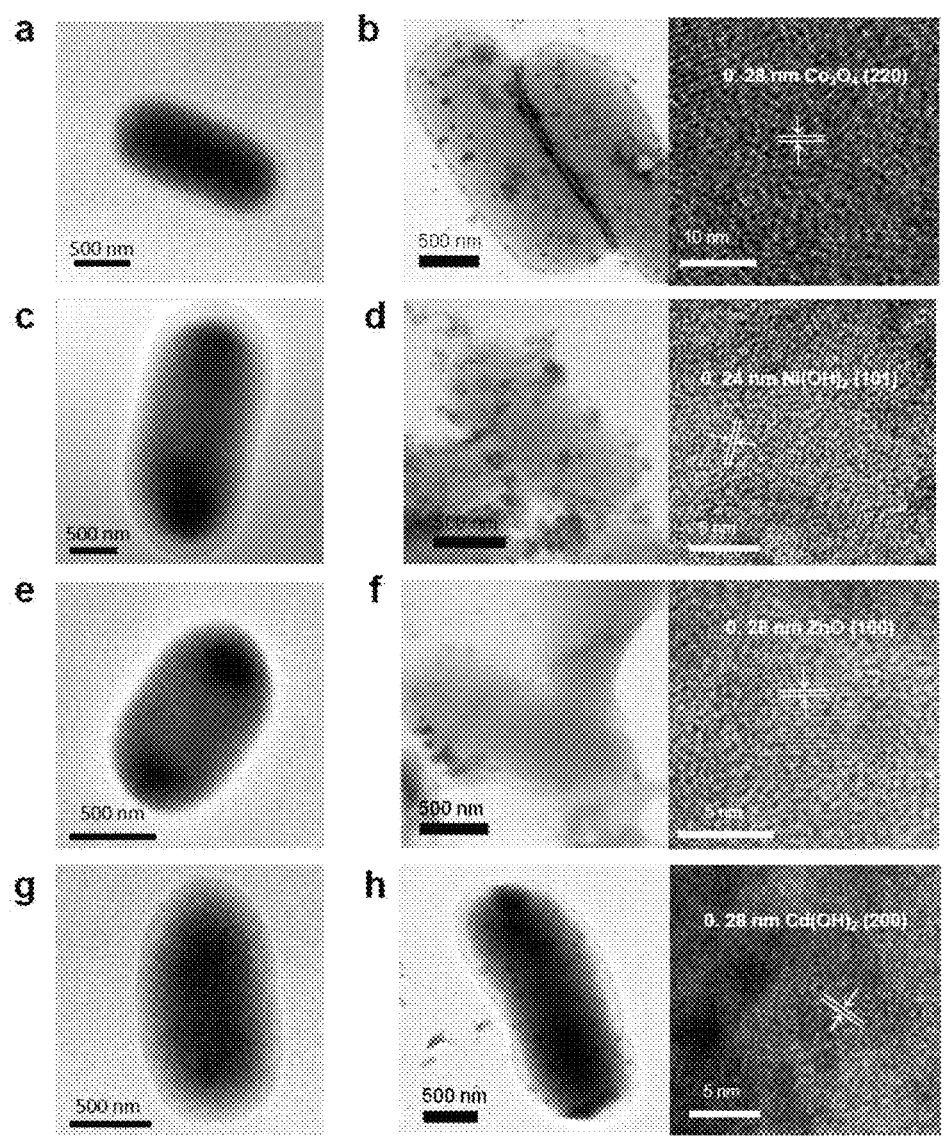
FIG. 21 shows the appearance of metal nanoparticles (a, c, e and g) synthesized using a recombinant microorganism without increasing the pH of media containing Co, Ni, Zn and Cd ions, and metal nanoparticles (b, d, f and h) synthesized using a recombinant microorganism after increasing the pH of media containing Co, Ni, Zn and Cd ions.

Example 6: Synthesis of Metal Nanoparticles Through Increase in pH of Medium In the case of some metals, it was shown that metal nanoparticles were not synthesized even when metal ions were added to the medium in which the recombinant microorganism produced in Example 1 had been cultured. In other words, one hour after inducing expression of metallothionein and phytochelatin synthase in the recombinant microorganism produced in Example 1 above by IPTG, cobalt (Co, $CoCl_2 6H_2O$, 0.5 mM), nickel (Ni, $NiCl_2 6H_2O$, 0.5 mM), zinc (Zn, $ZnSO_4 7H_2O$, 0.5 mM) or cadmium (Cd, $CdCl_2$, 0.5 mM) ions, were added to the LB liquid medium (Tryptone 10 g/L, yeast extract 5 g/L, NaCl 5 g/L, pH 6.5) in which the recombinant E. coli strain has been cultured, after which the recombinant microorganism was additionally cultured for 12 hours. The culture was centrifuged at 3500 rpm and 4° C. for 15 minutes, after which the supernatant was discarded and the E. coli pellet was collected. The E. coli pellet was washed three times with PBS buffer, and then dried in a freeze-dryer under vacuum for one day or more. In this procedure, whether nanoparticles would be synthesized was examined by transmission electron microscopy (TEM) (Tecnai F20, Philips, Netherlands), but the shape of synthesized nanoparticles could not be observed, and only the appearance of the recombinant E. coli was observed (FIG. 21, in images (a), (c), (e), and (g)).

Figure 22:
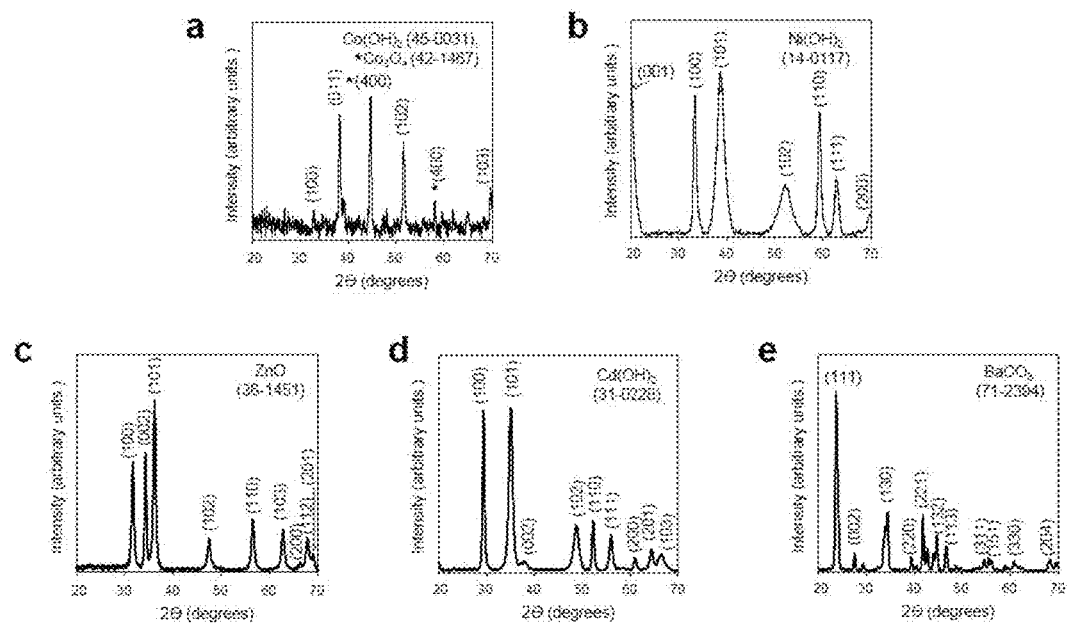
FIG. 22 shows X-ray diffraction graphs of metal nanoparticles using a recombinant microorganism after increasing the pH of media.

Accordingly, assuming that the ability of enzyme to bind to metal may vary depending on a change in pH, the present inventors changed pH to induce the synthesis of metal nanoparticles. In other words, one hour after inducing expression of metallothionein and phytochelatin synthase in the recombinant microorganism produced in Example 1 above by IPTG, the initial pH of the LB liquid medium (Tryptone 10 g/L, yeast extract 5 g/L, NaCl 5 g/L, pH 6.5) in which the recombinant E. coli strain has been cultured is increased to 7.5, and then cobalt (Co, $CoCl_2 6H_2O$, 0.5 mM), nickel (Ni, $NiCl_2 6H_2O$, 0.5 mM), zinc (Zn, $ZnSO_4 7H_2O$, 0.5 mM) or cadmium (Cd, $CdCl_2$, 0.5 mM) ions were added to the LB liquid medium, after which the recombinant microorganism was additionally cultured for 12 hours. After 12 hours of the culture, the pH of the medium was increased to 8 to 8.5. Thereafter, the culture was centrifuged at 3500 rpm and 4° C. for 15 minutes, after which the supernatant was discarded and the E. coli pellet was collected. The E. coli pellet was washed three times with PBS buffer, and then dried in a freeze-dryer under vacuum for one day or more. In this procedure, whether metal nanoparticles would be synthesized was examined by transmission electron microscopy (TEM)(Tecnai F20, Philips, Netherlands), and as a result, it could be seen that metal nanoparticles were synthesized, and particularly, the synthesized metal nanoparticles were crystalline (FIGS. 21b, 21d, 21f and 21h). The crystal structures of these metal nanoparticles were examined by X-ray diffraction analysis ((D/MAX-2,500, Rigaku, Japan) with CuKa radiation ($\lambda$=1.5406 Å)), and as a result, it was shown that when cobalt (Co), nickel (Ni), zinc (Zn) or cadmium (Cd) ions were added, cobalt oxide ($Co_3O_4$), nickel hydroxide ($Ni(OH)_2$), zinc oxide peroxide (ZnO) or cadmium hydroxide ($Cd(OH)_2$) metal nanoparticles were produced (FIG. 22).

Figure 23:
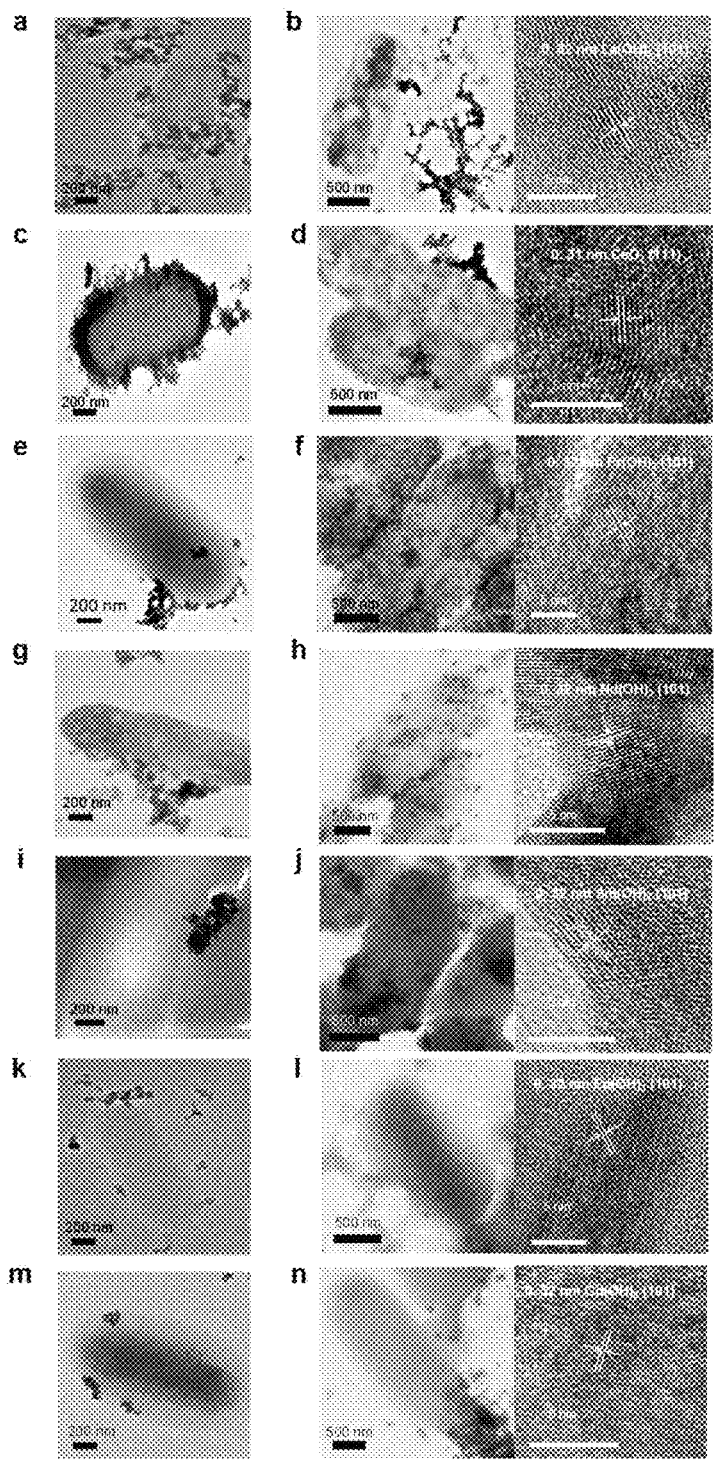
FIG. 23 shows the appearance of amorphous metal nanoparticles (a, c, e, g, i, k and m) synthesized using a recombinant microorganism without increasing the pH of media containing La, Ce, Pr, Nd, Sm, Eu and Gd ions, and crystalline metal nanoparticles (b, d, f, h, j, l and n) synthesized using a recombinant microorganism after increasing the pH of media containing La, Ce, Pr, Nd, Sm, Eu and Gd ions.

Example 7: Synthesis of Crystalline Metal Nanoparticles Through Increase in pH of Medium One hour after inducing expression of metallothionein and phytochelatin synthase in the recombinant microorganism produced in Example 1 above by IPTG, lanthanum (La, $La(NO_3)_3 6H_2O$, 0.5 mM), cerium (Ce, $Ce(NO_3)_3 6H_2O$, 0.5 mM), praseodymium (Pr, $Pr(NO_3)_3 6H_2O$, 0.5 mM), neodymium (Nd, $Nd(NO_3)_3 6H_2O$, 0.5 mM), samarium (Sm, $Sm(NO_3)_3 6H_2O$, 0.5 mM), europium (Eu, $Eu(NO_3)_3 6H_2O$, 0.5 mM) or gadolinium (Gd, Gd(NO$_3$)$_3$6H$_2$O, 0.5 mM) ions were added to the LB liquid medium (Tryptone 10 g/L, yeast extract 5 g/L, NaCl 5 g/L, pH 6.5) in which the recombinant *E. coli* strain has been cultured, after which the recombinant microorganism was additionally cultured for 12 hours. The culture was centrifuged at 3500 rpm and 4° C. for 15 minutes, after which the supernatant was discarded and the *E. coli* pellet was collected. The *E. coli* pellet was washed three times with PBS buffer, and then dried in a freeze-dryer under vacuum for one day or more. In this procedure, whether nanoparticles would be synthesized was examined by transmission electron microscopy (TEM) (Tecnai F20, Philips, Netherlands), but it was shown that synthesized nanoparticles were all amorphous, and crystalline nanoparticles were not synthesized (FIG. 23, images (a), (c), (e), (g), (i), (k), and (m)).

Accordingly, based on the fact that adjustment of the initial pH of the medium in the metal nanoparticle synthesis step induced the synthesis of crystalline metal nanoparticles which have not been synthesized, the present inventors adjusted the initial pH of the medium in the metal nanoparticle synthesis step.

Figure 24:
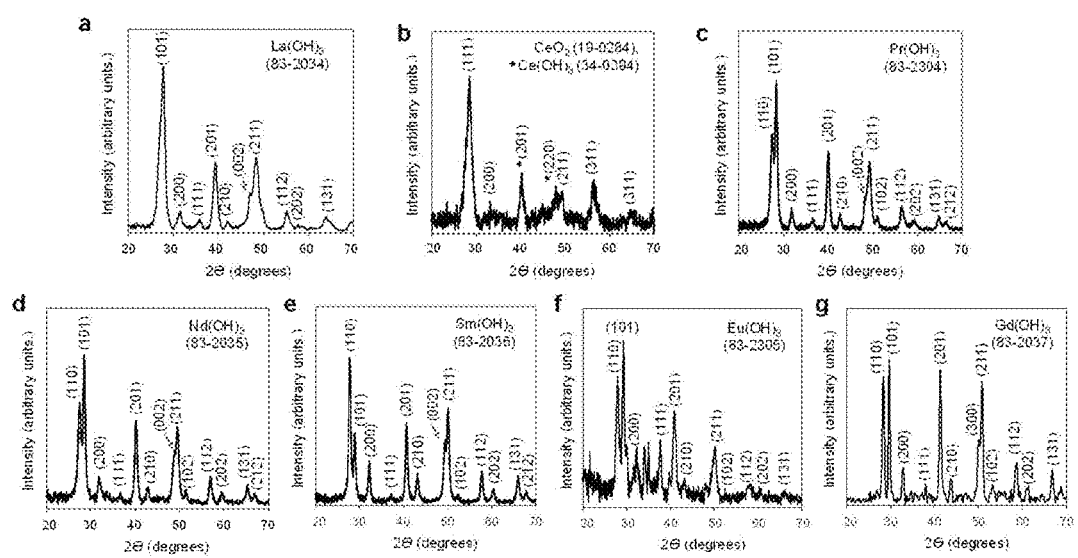
FIG. 24 shows X-ray diffraction graphs of crystalline metal nanoparticles synthesized using a recombinant microorganism after increasing the pH of media.

In other words, one hour after inducing expression of metallothionein and phytochelatin synthase in the recombinant microorganism produced in Example 1 above by IPTG, the initial pH of the LB liquid medium (Tryptone 10 g/L, yeast extract 5 g/L, NaCl 5 g/L' pH 6.5) in which the recombinant *E. coli* strain has been cultured is increased to 7.5, and then lanthanum (La, La(NO$_3$)$_3$6H$_2$O, 0.5 mM), cerium (Ce, Ce(NO$_3$)$_3$6H$_2$O, 0.5 mM), praseodymium (Pr, Pr(NO$_3$)$_3$6H$_2$O, 0.5 mM), neodymium (Nd, Nd(NO$_3$)$_3$6H$_2$O, 0.5 mM), samarium (Sm, Sm(NO$_3$)$_3$6H$_2$O, 0.5 mM), europium (Eu, Eu(NO$_3$)$_3$6H$_2$O, 0.5 mM), or gadolinium (Gd, Gd(NO$_3$)$_3$6H$_2$O, 0.5 mM) ions were added to the LB liquid medium, after which the recombinant microorganism was additionally cultured for 12 hours. After 12 hours of the culture, the pH of the medium was increased to 8 to 8.5. Thereafter, the culture was centrifuged at 3500 rpm and 4° C. for 15 minutes, after which the supernatant was discarded and the *E. coli* pellet was collected. The *E. coli* pellet was washed three times with PBS buffer, and then dried in a freeze-dryer under vacuum for one day or more. In this procedure, whether nanoparticles would be synthesized was examined by transmission electron microscopy (TEM)(Tecnai F20, Philips, Netherlands), and as a result, it could be seen that amorphous metal nanoparticles were synthesized before pH adjustment, but crystalline metal nanoparticles were synthesized as a result of pH adjustment (FIG. 23, images (b), (d), (f), (j), (l), and (n)). In addition, the crystal structures of the synthesized crystalline metal nanoparticles were examined by X-ray diffraction analysis ((D/MAX-2,500, Rigaku, Japan) with CuKa radiation ($\lambda$=1.5406 Å)) (FIG. 24), and as a result, it was observed that when lanthanum (La), cerium (Ce), praseodymium (Pr), neodymium (Nd), samarium (Sm), europium (Eu) or gadolinium (Gd) ions were added, crystalline metal particles of lanthanum hydroxide (La(OH)$_3$), cerium oxide (CeO$_2$), praseodymium hydroxide (Pr(OH)$_3$), neodymium hydroxide (Nd(OH)$_3$), samarium hydroxide (Sm(OH)$_3$), europium hydroxide (Eu(OH)$_3$) or gadolinium hydroxide (Gd(OH)$_3$) were produced (FIG. 24).

INDUSTRIAL APPLICABILITY

According to the present invention, a method for synthesizing metal nanoparticles is provided which have been difficult to synthesize by conventional biological methods. The present invention makes it possible to synthesize metal nanoparticles in an environmentally friendly and cost-effective manner, and also makes it possible to synthesize metal sulfide nanoparticles. In addition, even metal nanoparticles which could have been produced by conventional chemical or biological methods are produced in a significantly increased yield by use of the method of the present invention. In addition, the magnetic properties, the electrochemical properties, and the catalytic activity of the synthesized nanoparticles are identified so that the present invention can be applied to various industrial field applications including photoelectronics, batteries, contrast agents, semiconductor device, electronic devices, biosensors, catalysts, medicines, cosmetics, energy storage applications.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for producing a single-element metal nanoparticles comprising the steps of:
   (a) culturing a recombinant microorganism into which a metallothionein-encoding gene and a phytochelatin synthase-encoding gene have been introduced, in a medium at pH of 6 to 7, to induce expression of metallothionein and phytochelatin synthase in the recombinant microorganism;
   (b) increasing pH of medium of step (a) to pH of 7.3 to 7.7, and adding to the medium a metal ion selected from the group consisting of zinc (Zn), nickel (Ni), cobalt (Co), cadmium (Cd), praseodymium (Pr), gadolinium (Gd), lanthanum (La), cerium (Ce), neodymium (Nd), samarium (Sm), and europium (Eu), followed by additional culturing,
   (c) after the additional culturing of step (b), increasing pH of the medium of step (b) to pH of 8.0 to 9.0, to produce single-element metal nanoparticles: and
   (d) recovering the produced single-element metal nanoparticles,
      where the recombinant microorganism is a recombinant bacterium.

2. The method of claim 1, wherein the metallothionein-encoding gene has the nucleotide sequence of SEQ ID NO: 1, and the phytochelatin synthase-encoding gene has the nucleotide sequence of SEQ ID NO: 2.

3. The method of claim 1, wherein in step (b) the initial pH of the medium is increased to pH of 7.4 to 7.6.

4. The method of claim 3, wherein the pH of the medium in step (a) is pH 6.4 to 6.6.

5. The method of claim 1, wherein the produced single-element metal nanoparticle has a crystalline structure.

6. The method of claim 1, wherein the produced metal nanoparticle is selected from the group consisting of cobalt oxide($Co_3O_4$), nickel hydroxide ($Ni(OH)_2$), zinc oxide (ZnO), cadmium hydroxide ($Cd(OH)_2$), cobalt hydroxide ($Co(OH)_2$), lanthanum hydroxide ($La(OH)_3$), cerium oxide ($CeO_2$), praseodymium hydroxide ($Pr(OH)_3$), neodymium hydroxide ($Nd(OH)_3$), samarium hydroxide ($Sm(OH)_3$), europium hydroxide ($Eu(OH)_3$), and gadolinium hydroxide ($Gd(OH)_3$).

7. The method of claim 1, wherein the produced single-element metal nanoparticles are selected from the group consisting of cobalt oxide ($Co_3O_4$), nickel hydroxide ($Ni(OH)_2$), zinc oxide (ZnO) and cadmium hydroxide ($Cd(OH)_2$).

8. The method of claim 5, wherein the produced single-element metal nanoparticles are selected from the group consisting of lanthanum hydroxide (La(OH)$_3$), cerium oxide (CeO$_2$), praseodymium hydroxide (Pr(OH)$_3$), neodymium hydroxide (Nd(OH)$_3$), samarium hydroxide (Sm(OH)$_3$), europium hydroxide (Eu(OH)$_3$), and gadolinium hydroxide (Gd(OH)$_3$).

9. The method of claim 1, wherein concentration of the metal ion added to the medium in step (b) is 5 mM to 0.01 mM.

10. The method of claim 1, wherein the recombinant microorganism is a recombinant *E. coli*.

11. The method of claim 10, wherein the culturing in step (a) is carried out for one hour, and the additional culturing in step (b) is carried out for 12 hours.

12. The method of claim 1, wherein in step (c) the pH of the medium of step (b) is increased to pH of 8.0 to 8.5.

13. The method of claim 1, wherein the metal ion cobalt, nickel, zinc, or cadmium ion.

14. The method of claim 1, wherein the metal ion is lanthanum, cerium, praseodymium, neodymium, samarium, europium, or gadolinium ion, and wherein the produced single-element metal nanoparticles are crystalline metal nanoparticles.

15. A method for producing single-element metal nanoparticles, comprising the steps of:
   (a) culturing a recombinant *E. coli* bacterium into which a metallothionein-encoding gene and a phytochelatin synthase-encoding gene have been introduced, in a medium at pH of 6 to 7, to induce expression of metallothionein and phytochelatin synthase in the recombinant *E. coli* bacterium, wherein the metallothionein-encoding gene has the nucleotide sequence of SEQ ID NO: 1 and the phytochelatin synthase-encoding gene has the nucleotide sequence of SEQ ID NO: 2;
   (b) increasing pH of the medium of step (a) to pH of 7.3 to of 7.7, and adding to the medium a metal ion selected from the group consisting of zinc (Zn), nickel (Ni), cobalt (Co), cadmium (Cd), praseodymium (Pr), gadolinium (Gd), lanthanum (La), cerium (Ce), neodymium (Nd), samarium (Sm), and europium (Eu), followed by additional culturing;
   (c) after the additional culturing of step (b), increasing pH of the medium of step (b) to pH of 8.0 to 9.0, to produce single-element metal nanoparticles; and
   (d) recovering the produced single-element metal nanoparticles.

\* \* \* \* \*

UNITED STATES PATENT AND TRADEMARK OFFICE
CERTIFICATE OF CORRECTION

PATENT NO. : 10,851,390 B2
APPLICATION NO. : 16/068475
DATED : December 1, 2020
INVENTOR(S) : Sang Yup Lee et al.

It is certified that error appears in the above-identified patent and that said Letters Patent is hereby corrected as shown below:

In the Specification

Column 7, Line 13: "zinc oxide peroxide (ZnO)" should be -- zinc oxide (ZnO) --.

Column 7, Line 57: "zinc oxide peroxide (ZnO)" should be -- zinc oxide (ZnO) --.

Column 18, Line 54: "zinc oxide peroxide (ZnO)" should be -- zinc oxide (ZnO) --.

Signed and Sealed this
Twelfth Day of January, 2021

Andrei Iancu
*Director of the United States Patent and Trademark Office*

SEQUENCE LISTING

<160> NUMBER OF SEQ ID NOS: 8

<210> SEQ ID NO 1
<211> LENGTH: 243
<212> TYPE: DNA
<213> ORGANISM: Pseudomonas putida KT2440

<400> SEQUENCE: 1

```
atgaacgatc accaccacca caacgatcaa cgctgcgcgt gtacgcactg ttcctgcact      60
gtggatgcca atgccttgca gcgcgacggc aaggcctatt gctgcgaggc ctgcgccagc     120
ggccaccgca agggtgagcc ctgccggatg caggactgcc attgtggtga gaagccgggc     180
gagagcgcgg tggacaatgc gttggatgaa accttcccag cgagtgatcc gatctcgccc     240
taa                                                                   243
```

<210> SEQ ID NO 2
<211> LENGTH: 1458

```
<212> TYPE: DNA
<213> ORGANISM: Arabidopsis thaliana

<400> SEQUENCE: 2
atggctatgg cgagtttata tcggcgatct cttccttctc ctccggccat cgactttct       60 tccgccgaag gcaagctaat cttcaatgaa gcgcttcaga aaggaactat ggaaggattt     120
ttcaggttga tttcgtattt tcagacacaa tccgaacctg cgtattgtgg tttggctagt     180
ctctcagtgg tgttgaatgc tctttctatc gatcctggac gtaaatggaa agggccttgg     240
aggtggtttg atgaatcaat gttggattgc tgcgaacctc tggaagtagt gaaggaaaaa     300
ggcatttcat ttggaaaagt tgtctgtttg gctcattgtt caggagcaaa agttgaggct     360
ttccgtacaa gtcagagcac cattgatgat tccgcaaat tgtcgtcaa atgcacgagt       420 tctgagaatt gtcatatgat ctcaacatat accgaggtg tatttaagca gactgggact      480
ggtcactttt cacctattgg tggctataat gctgagagag atatggcttt gattcttgat     540
gttgctcgtt tcaagtatcc ccctcactgg gttcctctta acttctttg ggaagccatg      600 gacagtattg atcagtcaac agggaaacgt agagggttca tgctcatatc tagaccacac     660
agagaacccg gattgctcta tactctgagc tgcaaggatg aaagctggat cgaaatagcc     720
aagtatttga aggaagatgt tcctcgtctt gtaagttcac agcatgtaga ttctgtggag     780
aaaatcatat cagttgtgtt caagtcactt ccatcaaatt tcaaccaatt catcagatgg     840
gtggctgaga tccgaattac agaggactca aaccaaaatc tcagcgcaga ggcgaagtct     900
aggctgaaac taaagcaatt ggtgctgaag gaagtgcacg aaactgaact gttcaaacac     960
atcaataagt tcttatccac agtgggttat gaagacagtc tgacttatgc tgctgcaaag    1020
gcttgttgcc aaggagctga aatcttatcc ggaagcccat caaaagagtt ttgttgtcgg    1080
gaaacttgcg tgaaatgcat caaaggtcct gatgactctg aaggcacggt ggtgaccgga    1140
gttgtggtgc gtgatgggaa tgaacaaaag gttgatctgt tagtgccatc gacgcaaact    1200
gagtgtgaat gtggtcctga agcaacttat ccagcaggaa acgatgtgtt cactgcactt    1260
ctattggctt tacctccaca gacatggtca gggatcaaag accaagctct tatgcatgaa    1320
atgaagcagc tcatttccat ggcttccctc ccaactttgc ttcaagaaga ggtattgcat    1380
cttcgacggc aacttcagct gctaaaacga tgccaagaga acaaggaaga ggatgatctc    1440
gctgctcctg cctattaa                                                  1458

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
atagaattca tgaacgatca ccaccaccac aac                                    33

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
tatctgcagt tagggcgaga tcggatcact c                                      31
```

```
<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5
atagaattca tggctatggc gagtttatat cgg                             33

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
tatgcatgct taataggcag gagcagcgag atc                             33

<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
atactgcagt tgacaattaa tcatcggctc gtata                           35

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
tatgcatgct taataggcag gagcagcgag a                               31
```